United States Patent
Yumioka et al.

(10) Patent No.: US 6,528,068 B1
(45) Date of Patent: Mar. 4, 2003

(54) COSMETIC COMPOSITION CONTAINING N-ACYL NEUTRAL AMINO ACID ESTERS OF LOWER ALCOHOLS

(75) Inventors: Ryosuke Yumioka, Kawasaki (JP); Hiroji Ishii, Kawasaki (JP); Masako Koyama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/219,777

(22) Filed: Dec. 23, 1998

(30) Foreign Application Priority Data

Dec. 25, 1997 (JP) .............................. 9-357422
Feb. 27, 1998 (JP) .............................. 10-047133
Apr. 22, 1998 (JP) .............................. 10-112294
Jul. 23, 1998 (JP) .............................. 10-207588

(51) Int. Cl.$^7$ ................................ A61K 6/00
(52) U.S. Cl. .................. 424/401; 424/59; 424/63; 514/558; 514/506; 514/509
(58) Field of Search ............... 424/401, 59, 63; 514/558, 506, 509

(56) References Cited

U.S. PATENT DOCUMENTS 3,969,087 A * 7/1976 Saito et al. ..................... 44/7
5,334,713 A * 8/1994 Hattori et al. ............... 540/113

FOREIGN PATENT DOCUMENTS

| DE | 2 260 640 | 6/1973 |
| DE | 2 234 399 | 1/1974 |
| DE | 2 246 433 | 4/1974 |
| EP | 0 839 515 | 5/1998 |
| EP | 0 913 390 | 5/1999 |
| JP | 04149111 A | * 5/1992 |
| WO | 94/15580 | * 7/1994 |

OTHER PUBLICATIONS

Derwent Publications, AN 1997–103674, JP 08 337562, Dec. 24, 1996.
A. Ishida, et al., Bulletin of the Chemical Society of Japan, vol. 51, No. 7, pps. 2077–2081, "Total Synthesis of (+) Variotin and its Analogs," Jul. 1978.

* cited by examiner

*Primary Examiner*—Thurman K. Page
*Assistant Examiner*—Lakshmi Channavajjala
(74) *Attorney, Agent, or Firm*—Oblon, Spivak, McClelland, Maier & Neustadt, P.C.

(57) ABSTRACT

An N-long-chain acyl neutral amino acid ester containing a straight-chain or branched-chain, saturated or unsaturated acyl group having from 6 to 22 carbon atoms, where the hydrocarbon group of the alcohol constituting the ester is a straight-chain or branched-chain, saturated or unsaturated hydrocarbon group having from 1 to 10 carbon atoms disclosed herein is an oily material suitable for cosmetic compositions, which provide an excellent feeling upon use and also an excellent hair conditioning effect to a cosmetic composition containing the same. An ultraviolet ray-absorbing composition containing the N-long-chain acyl neutral amino acid ester or/and an N-long-chain acyl acidic amino acid diester is provided, which also has excellent feel. An inorganic pigment composition containing the N-long-chain acyl neutral amino acid ester or/and the above-mentioned N-long-chain acyl acidic amino acid diester is also provided, which has excellent dispersion (stability) of the inorganic pigment, is less irritating to the skin, has excellent feel upon use and is not sticky.

17 Claims, No Drawings

US 6,528,068 B1

COSMETIC COMPOSITION CONTAINING N-ACYL NEUTRAL AMINO ACID ESTERS OF LOWER ALCOHOLS

TECHNICAL FIELD

Disclosed here in the present specification are a group of inventions so linked as to form a single general inventive concept, with respect to various uses of specific N-long-chain acyl neutral amino acid esters and specific N-long-chain acyl acidic amino acid diesters as active ingredients of cosmetic compositions.

A first invention of such a group of inventions (hereinafter, referred to as "the first invention") relates to an oily ingredient of cosmetics which is formed of a specific N-long-chain acyl neutral amino acid ester, and a cosmetic composition characterized by containing the same. More specifically, it relates to an oily material(or oily ingredient) of cosmetics which is formed of an N-long-chain acyl neutral amino acid ester where the hydrocarbon group of the alcoholic moiety is a straight-chain or branched-chain, saturated or unsaturated hydrocarbon group having from 1 to 10 carbon atoms. (In other words, the hydrocarbon residue of the alcoholic moiety constituting such N-long-chain acyl neutral amino acid ester is a straight-chain or branched-chain, saturated or unsaturated hydrocarbon group with 1 to 10 carbon atoms.) It also relates to a cosmetic composition characterized by containing the same.

A second invention of such a group of inventions (hereinafter, referred to as "the second invention") relates to an ultraviolet ray-absorbing composition. More specifically, it relates to an ultraviolet ray-absorbing composition characterized by containing an ultraviolet rays absorbent (i.e., an ultraviolet rays absorbing agent) and an N-long-chain acyl neutral amino acid ester or/and an N-long-chain acyl acidic amino acid diester as active ingredient(s). This ultraviolet ray-absorbing composition includes, as an embodiment thereof, a cosmetic composition.

And, a third invention of such a group of inventions (hereinafter, referred to as "the third invention") relates to an inorganic pigment composition. More specifically, it relates to an inorganic pigment composition characterized by containing an inorganic pigment and an N-long-chain acyl neutral amino acid ester or/and an N-long-chain acyl acidic amino acid diester as active ingredient(s). This inorganic pigment composition includes, as an embodiment thereof, a cosmetic composition.

BACKGROUND ART

First, the background art on the first invention is as follows.

In cosmetic compositions, an oily material is widely used as a binder for the components, an emollient or the like, or for providing a hair conditioning property. As an oily material for a cosmetic composition, mineral oils such as liquid paraffin and the like, and fatty acid esters such as IPM (isopropyl myristate) and IPP (isopropyl palmitate) have been widely used so far.

Further, an example in which amino acid derivatives are used as an oily material has been known. For example, Japnese patent publication (kokoku) No. 12908/1979 discloses an ester of an N-long-chain acyl neutral amino acid and a higher alcohol having from 12 to 30 carbon atoms as an oil-soluble surfactant which is suitable in the field of fragrances.

However, these oily materials for cosmetics have involved problems that the oily materials when formulated in cosmetic compositions may impair the feeling upon use of the cosmetic composition owing to an unpleasant oily feeling or stickiness peculiar to such oily material. Further, a hair conditioning effect has not been satisfactory. Accordingly, an oily material for cosmetics which is better in these points has been in great demand.

By the way, as an N-long-chain acyl neutral amino acid ester, an amino acid ester with a long-chain alcohol has been known as described in the Jap. pat. Publn. (kokoku) No. 12908/1979. However, with respect to an amino acid ester with a shorter-chain alcohol, examples in which it is actually synthesized and studied for use in cosmetics have been hardly known. As a specific example, it is only disclosed on page 167, lower column to page 168, left upper column of the Jap. pat. Publn. (kokoku) No. 129078/1979 that N-2-ethylhexanoyl-N-methyl-β-alanine.methyl ester is tested and its compatibility with an oily solvent is poor. Thus, an ester of an N-long-chain acyl neutral amino acid and a short-chain alcohol has not been used at all as an oily material for cosmetics.

However, in recent years, owing to the advancement of a blending technique, an emulsifying equipment and the like, the problem of such compatibility is rather considered less serious, and an important subject is how to satisfy consumers' various needs and higher levels of needs.

Accordingly, it is an object of the invention to provide an oily material for cosmetics which is improved in an oily feeling or stickiness, which has an excellent feeling upon use of a cosmetic composition and also in a hair conditioning effect, and further to provide a cosmetic composition containing the same.

Next, the background concerning the second invention is as follows.

Ultraviolet rays are known to give various changes to the skin. In the field of dermatology, ultraviolet rays are classified into long-wave ultraviolet ray (400 to 320 nm), medium-wave ultraviolet ray (320 to 290 nm) and short-wave ultraviolet ray, which are called UV-A, UV-B and UV-C in this order, respectively. Of these, UV-C is absorbed in the ozone layer, and scarcely reaches the earth. Further, with respect to UV-B, it is known that when the skin is irradiated with more than its certain amount, an erythema or a blister is formed or pigmentation occurs. Meanwhile, it has been so far said that UV-A does not change the skin so much. However, it has recently been found through an electron microscope or from a histological evaluation that UV-A changes the elastic fibers in the blood vessel wall or the connective tissue, or damages the sensitive skin. Moreover, it has been reported that UV-A accelerates the activity of UV-B (J. Invest. Derm. 59 (6), 416 (1973)). Accordingly, it is important to cut UV-A. For these reasons, cosmetics or skin medicines for external application often contain an ultraviolet rays absorbent (UV absorbent) as an ultraviolet ray cutting agent (UV cutting agent).

As UV-A absorbents which have been lately highlighted, for example, 4-t-butyl-4'-methoxybenzoylmethane and 2-ethylhexyl dimethoxybenzylidenedioxoimidazolidinepropionate (with respect to the latter, see Japanese patent application laid-open (kokai) No. 101371/1988) can be mentioned. These are solids which are sparingly soluble in water and oil(with respect to the former, see Jap. pat. appln. Laid-open (kokai) No. 291019/1997). The sparingly-soluble UV absorbents involve problems that sufficient amounts thereof cannot be incorporated in cosmetics or the like, and when these UV absorbents are once incorporated, crystals thereof are precipitated in cosmetics or skin medicines for external application during the storage, i.e., the stability thereof is therefore poor. Especially in the latter case, appropriate solvents are limited in their type.

The ultraviolet rays are harmful to (the skin of) humans. Moreover, of plastics, emulsion paints, oil paints, coating agents and the like, there are some components thereof which undergo degradation by ultraviolet rays, and deterioration is prevented by incorporating an ultraviolet ray absorbent in such products. The foregoing problems associated with the sparingly-soluble UV absorbent also occur with respect to the use in such plastics and the like other than the skin of humans.

By the way, an oil is incorporated into cosmetics containing a UV absorbent in order to prevent the UV absorbent from flowing down due to sweat or water. However, there is a problem that when an oil is incorporated into cosmetics or skin medicines for external application, stickiness is provided.

Accordingly, under these circumstances of the conventional art, it is an object of the present invention is to provide an ultraviolet rays absorbing composition usable as a cosmetic composition, which is excellent in the lack of a stickiness, which is less irritates the skin, and in which a sparingly-soluble UV absorbent, when used, can stably be incorporated at a high concentration And finally, the background concerning the third invention is as follows.

An inorganic pigment is, as well known, ordinarily used in cosmetics, paints, resins, ink, rubbers, pencils and the like. For example, in cosmetics, an inorganic pigment is incorporated to impart, to products, characteristics such as extensibility, adhesion, film-strength power and the like, to maintain forms of products or to color the same.

When an inorganic pigment is used for these purposes, it is required that the inorganic pigment is uniformly dispersed in a composition and a composition free from unevenness of a color or the like and having high dispersion stability is provided. However, since inorganic pigments are less compatible with an oil, it is difficult to obtain a better dispersion state because of the influence of the oily material in the composition. For example, even when an oily material having a relatively high polarity, such as lanoline, isopropyl myristate, a fatty acid higher alcohol ester or the like is used in cosmetics, it is difficult to obtain a satisfactory dispersibility.

Thus, in a composition containing an oily material (i.e., oily ingredient) and an inorganic pigment, there are problems that a relatively large amount of an oily material has to be added for dispersing the inorganic pigment and that when an inorganic pigment is used in cosmetics, for example, the feeling upon use is notably decreased because of an unpleasant oily feeling or stickiness peculiar to the oily material.

Accordingly, in such background of the conventional art, it is an object of the present invention to provide an inorganic pigment composition usable as a cosmetic composition which is excellent in dispersibility (stability) of an inorganic pigment, which is less irritative to the skin, when used in cosmetics, and which exhibits a good feeling upon use.

DISCLOSURE OF THE INVENTION

In view of the background of the first invention, the present inventors have assiduously conducted investigations, and has consequently found that an N-long-chain acyl neutral amino acid ester where the hydrocarbon group of the alcohol constituting the ester is a hydrocarbon group having from 1 to 10 carbon atoms, has a dry or clean feeling although it is an oily material, exhibits an improved feeling upon use onto the skin, such as extensibility, adaptability, smoothness or the like in addition to the clean feeling, and is further excellent in hair conditioning effect. These findings have led to the completion of the present invention.

Accordingly, the first invention relates to an oily material usable as a cosmetic composition which is formed of an N-long-chain acyl neutral amino acid ester containing an acyl group having from 6 to 22 carbon atoms, where the hydrocarbon group of the alcohol constituting the ester is a hydrocarbon group having from 1 to 10 carbon atoms. Further, the invention relates to a cosmetic composition characterized by containing such oily material.

Now, the invention will be described in greater detail below.

The long-chain acyl group of an N-long-chain acyl neutral amino acid ester of the present invention is a straight-chain or branched-chain, saturated or unsaturated acyl group having from 6 to 22 carbon atoms. Examples thereof include those acyl groups which can be derived from capric acid, lauric acid, myristic acid, palmitic acid, stearic acid, behenic acid, linoleic acid, linolenic acid, oleic acid, isostearic acid, 2-ethylhexanoic acid, coconut oil fatty acid, tallow fatty acid, hardened tallow fatty acid, palm kernel oil fatty acid, and the like. Preferable examples of the acyl group include a caproyl group, a lauroyl group, a myristoyl group, a palmitoyl group, a stearoyl group, a behenoyl group, a coconut oil fatty acid acyl group, a hardened tallow fatty acid acyl group and the like.

Further, examples of the neutral amino acids constituting the neutral amino acid moiety include neutral amino acids such as glycine, alanine, valine, leucine, isoleucine, serine, threonine, proline, β-alanine, aminobutyric acid, sarcosine, N-methyl-β-alanine and the like. Preferable are glycine, alanine, valine, leucine, isoleucine, β-alanine, α-aminobutyric acid, γ-aminobutyric acid, sarcosine and N-methyl-β-alanine. More preferable are glycine, alanine, β-alanine, α-aminobutyric acid, γ-aminobutyric acid, sarcosine and N-methyl-β-alanine. Furthermore preferable are sarcosine, alanine, glycine and N-methyl-β-alanine. Especially preferable are N-alkyl neutral amino acids. Most preferable are sarcosine and N-methyl-β-alanine. These amino acids may be optically active compounds or racemic compounds.

And, the hydrocarbon group of the alcohol constituting the ester is a branched-chain or straight-chain alkyl or alkenyl group having from 1 to 10 carbon atoms. The alkyl group is preferable. Examples thereof include hydrocarbon groups which can be derived from ethanol, propanol, isopropanol, butanol, t-butanol, isobutanol, 3-methyl-1-butanol, 2-methyl-1-butanol, fusel oil, pentanol, hexanol, cyclohexanol, octanol, 2-ethylhexanol and decanol. A methyl ester having 1 carbon atom is undesirable because it means that methanol is used as a starting material.

Further, a branched-chain or straight-chain alkyl group having from 2 to 8 carbon atoms is preferable from the standpoint of feeling upon use. Especially, a branched-chain or straight-chain alkyl group having from 2 to 5 carbon atoms is preferable because a dry or clean feeling is excellent and the effects of the present invention are exhibited more satisfactorily. Still further, a branched-chain alkyl group having from 3 to 5 carbon atoms is preferable from the aspect of the stability against hydrolysis in addition to the feeling upon use and the like. Examples thereof include an isopropyl group, a t-butyl group, an isobutyl group and the like. Of these, an isopropyl group is most preferable.

When preferable examples of the N-long-chain acyl neutral amino acid ester of the present invention are represented by the general formula, those represented by Formula (1) below can be mentioned.

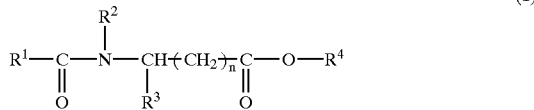

(1)

wherein $R^1$ represents a branched-chain or straight-chain alkyl or alkenyl group having from 5 to 21 carbon atoms, $R^2$ represents a hydrogen atom or a straight-chain or branched-chain alkyl group having from 1 to 3 carbon atoms, $R^3$ represents a hydrogen atom or a straight-chain or branched-chain alkyl group having from 1 to 4 carbon atoms, $R^4$ represents a branched-chain or straight-chain alkyl or alkenyl group having from 1 to 10 carbon atoms, and n is an integer of from 0 to 2.

In Formula (1), preferable examples of the acyl group ($R^1$—CO—) and the hydrocarbon group $R^4$ of the alcohol constituting the ester have been mentioned above. Preferable examples of the neutral amino acid moiety have also been mentioned above. As $R^2$ is more preferable a hydrogen atom or a methyl group, and most preferably a methyl group. As $R^3$ is preferable a hydrogen atom or a methyl group, and most preferably a hydrogen atom. As n is more preferable an integer of 0 or 1.

In this connection, it is to be noted that those N-long-chain acyl neutral amino acid esters which are represented by Formula (1) are novel compounds.

The N-long-chain acyl neutral amino acid ester of the present invention can be obtained by, for example, esterifying an N-long-chain acyl neutral amino acid and an alcohol through heat-dehydrocondensation under atmospheric pressure or reduced pressure. Further, it can also be obtained by an azeotropic dehydrocondensation reaction using a solvent such as toluene or the like (see Synthesis Examples 5, 6 and the like to be described later) or by transesterification reaction. An N-long-chain acyl neutral amino acid or an alcohol to be used to synithesize the N-long-chain acyl neutral amino acid ester are not necessarily single compounds, and they may be a mixture of N-long-chain acyl neutral amino acids containing different acyl groups and/or neutral amino acids and a mixture of alcohols which are different in the chain length or the like.

The resulting N-long-chain acyl neutral amino acid ester can be used after purification by a known method which those skilled in the art commonly use, such as distillation, extraction, chromatography or the like. Incidentally, with respect to the N-long-chain acyl neutral amino acid and its salt which are starting materials in the production, the alcohol and the like acceptable in a cosmetic composition, and further, the starting neutral amino acid and the like and by-product fatty acids and the like which may accompany the N-long-chain acyl neutral amino acid and its salt, they are ordinarily used in the cosmetic composition, and therefore, may be contained in the N-long-chain acyl neutral amino acid ester unless the effects of the present invention are impaired.

By the way, N-long-chain acyl neutral amino acid can be produced by a known method, for example, the so-called Schotten-Bauman reaction (see Japanese patent publication (kokoku) No. 38681/1976 and the like) in which a long-chain fatty acid halide is reacted with an amino acid in the presence of a basic catalyst.

The oily material for cosmetic compositions of the present invention can be used as an oily ingredient for various cosmetic compositions such as skin care product, hair care product and the like, and it can be formed into cosmetic compositions of the present invention. As such cosmetic composition can be mentioned various cosmetic compositions, such as washing cream, washing foam, cleansing cream, massage cream, cold cream, moisture cream, milky lotion, lotion, hand cream, pack, men's skin care product, foundation, lipstick, press powder, eye shadow, hair oil or cream in stick from, hair liquid, setting lotion, permanent wave liquid, hair cream, hair lotion, hair mousse, shampoo, hair rinse, hair conditioner, body shampoo, solid detergent, liquid detergent, antiperspirant, after-shave cream, anti-sunburn cream, anti-sunburn oil, bath product, hair dye and the like. The form of the cosmetic compositions is not particularly limited. Any formmay be taken. Examples thereof include an emulsion form, a solution form, a soluble form, a powder dispersion form, a water-oil two-layer form, a water-oil-powder three-layer form and the like.

The cosmetic composition of the present invention can contain any other oily materials or ingredients which are usable in cosmetics unless the effects of the present invention are impaired. Examples of such materials can include oily materials derived from animals and plants, such as saturated or unsaturated fatty acids and higher alcohols obtained therefrom, squalane, castor oil and derivatives thereof, bees wax, lanolines including liquid and purified lanolines and derivatives thereof, cholesterol and derivatives thereof, academian nut oil, jojoba oil, carnauba wax, sesame oil, cocoa oil, palm oil, mink oil, Japan wax, candelilla wax, whale oil and the like; oily materials derived from petroleum and mineral, such as paraffin, microcrystalline wax, liquid paraffin, vaseline, ceresine and the like; silicones, for example, silicone polymers such as methylpolysiloxane, polyoxyethylene.methylpolysiloxane, polyoxypropylene.methylpolyoxysiloxane, poly(oxyethylene, oxypropylene).methylpolysiloxane, methylphenylpolysiloxane, fatty acid-modified polysiloxane, fatty alcohol-modified polysiloxane, amino acid-modified polysiloxane and the like; a resin acid; a fatty acid ester; ketones and the like. Since the N-acyl neutral amino acid ester of the present invention is also effective for improving stickiness and the like of the other oily materials, the effects of the present invention can satisfactorily be exhibited also in cosmetic compositions containing such other ordinary oily materials.

Further, the cosmetic composition of the present invention can contain one or more surfactants insofar as the effects of the present invention are not impaired. Examples thereof include anionic surfactants such as, e.g., N-long-chain acyl amino acid salts such as N-long-chain acyl acidic amino acid salts and N-long-chain acyl neutral amino acid salts, N-long-chain fatty acid acyl-N-methyltaurine salts, alkyl sulfates, and alkylene oxide adducts thereof, fatty acid amide ether sulfates, fatty acid metal salts and weak base salts, sulfosuccinic acid-type surfactants, alkyl phosphates, and alkylene oxide adducts thereof, and alkyl ether carboxylic acids; nonionic surfactants such as, e.g., ether-type surfactants such as glycerol ethers, and alkylene oxide adducts thereof and the like, ester-type surfactants such as glycerol esters, and alkylene oxide adducts thereof and the like, ether ester-type surfactants such as sorbitan esters, and alkylene oxide adducts thereof and the like, ester-type surfactants such as polyoxyalkylene fatty acid esters, glycerol esters, fatty acid polyglycerol esters, sorbitan esters, sucrose fatty acid esters and the like, alkyl glycosides, nitrogen-containing nonionic surfactants such as hardened castor oil pyroglutamic acid diesters, and ethylene oxide adducts thereof, fatty acid alkanol amides and the like; cationic surfactants, for example, aliphatic amine salts such as alkylammonium chlorides, dialkylammonium chlorides and the like, and quaternary ammonium salts thereof, aromatic quaternary ammonium salts such as benzalkonium salts and the like, and fatty acid acylarginine esters; and amphoteric surfactants, for example, betaine-type surfactants such as carboxybetaine and the like, aminocarboxylic acid-type surfactants, and imidazoline-type surfactants.

Moreover, the cosmetic composition of the invention can contain, other than those surfactants mentioned above, various additives which are ordinarily used in a cosmetic composition unless the effects of the invention are impaired. Examples thereof include amino acids such as glycine, alanine, serine, threonine, arginine, glutamic acid, aspartic acid, leucine, valine and the like; polyhydric alcohols such as glycerol, ethylene glycol, 1,3-butylene glycol, propylene glycol, isoprene glycol and the like; water-soluble high-molecular compounds such as polyamino acids including polyglutamic acid and polyaspartic acid, and salts thereof, polyethylene glycol, gum arabic, alginates, xanthane gum, hyaluronic acid, hyaluronates, chitin, chitosan, water-soluble chitin, carboxyvinyl polymer, carboxymethyl cellulose, hydroxyethyl cellulose, hydroxypropyltrimethylammonium chloride, poly-(dimethylmethylenepiperidium chloride), polyvinylpyrolidone derivative quaternary ammonium salt, cationic protein, collagen hydrolyzate, and derivatives thereof, acylated protein, polyglycerol and the like; sugar alcohols such as mannitol and the like, and alkylene oxide adducts thereof; and lower alcohols such as ethanol, propanol and the like. Further, extracts of animals and plants, nucleic acids, vitamins, enzymes, anti-inflammatory agents, disinfectants, antiseptics, antioxidants, ultraviolet rays absorbents, chelating agents, antiperspirants, pigments, coloring matters, oxidation colors, organic and inorganic powders, pH modifiers, pearlescent agents, wetting agents and the like can also be contained.

The amount of an N-long-chain acyl neutral amino acid ester of the present invention to be incorporated into a cosmetic composition, varies depending on the form of a product, and it is not particularly limited. It is commonly used in the range of 0.01% by weight or more. The preferable range is between 0.1 and 50% by weight in case of a skin cosmetic composition. It can preferably be between 0.1 and 30% by weight in case of a hair cosmetic composition.

Further, in view of the background on the second invention, the present inventors have assiduously conducted investigations, and have consequently found that the above-mentioned problems can be solved by, when incorporating a UV absorbent into cosmetics or the like, using a specific N-long-chain acyl neutral amino acid ester or N-long-chain acyl acidic amino acid diester, together with the UV absorbent. These findings have led to the completion of the invention.

Accordingly, the second invention relates to an ultraviolet ray-absorbing composition characterized by containing, as active ingredients, an ultraviolet ray absorbent, and (A) an N-long-chain acyl neutral amino acid ester containing a straight-chain or branched-chain, saturated or unsaturated acyl group having from 6 to 22 carbon atoms, where the hydrocarbon group of the alcohol constituting the ester is a straight-chain or branched-chain, saturated or unsaturated hydrocarbon group having from 1 to 10 carbon atoms or/and (B) an N-long-chain acyl acidic amino acid diester containing a straight-chain or branched-chain, saturated or unsaturated acyl group having from 6 to 22 carbon atoms, where the hydrocarbon group of the alcohol constituting the ester is a straight-chain or branched-chain, saturated or unsaturated hydrocarbon group having from 1 to 10 carbon atoms.

Incidentally, the two types of the esters mentioned above are less irritative to the skin and can be an excellent oily material (oily agent) of cosmetic composition or the like.

Now, the second invention will be described in greater detail below.

First, UV absorbents, one of the ingredients of the ultraviolet ray-absorbing composition of the present invention will be described.

As UV absorbents for cosmetics or the like, a large number of ultraviolet ray absorbents have been developed. Examples thereof include benzophenone-type ultraviolet ray absorbents such as 2-hydroxy-4-methoxybenzophenone, 2-hydroxy-4-methoxybenzophenone 5-sulfonic acid, sodium 2-hydroxy-4-methoxybenzophenone-5-sulfonate, dihydroxydimethoxybenzophenone, sodium dihydroxydimethoxybenzophenonesulfonate, 2,4-dihydroxybenzophenone, tetrahydroxybenzophenone and the like; para-aminobenzoic acid-type ultraviolet ray absorbents such as para-aminobenzoic acid (PABA), ethyl para-aminobenzoate, glyceryl para-aminobenzoate, amyl para-dimethylaminobenzoate, octyl para-dimethylaminobenzoate and the like; cinnamic acid-type ultraviolet ray absorbents such as ethyl para-methoxycinnamate, isopropyl para-methoxycinnamate, octyl para-methoxycinnamate, 2-ethoxyethyl para-methoxycinnamate, sodium para-methoxycinnamate, potassium para-methoxycinnamate, mono-2-ethylhexanoic acid glyceryl para-methoxycinnamate; and salicylic acid-type ultraviolet ray absorbents such as octyl salicylate, phenyl salicylate, homomethyl salicylate, dipropylene glycol salicylate, ethylene glycol salicylate, myristyl salicylate, methyl salicylate and the like, as well as urocanic acid, ethyl urocanate, 4-t-butyl-4'-methoxydibenzoylmethane ("Parsol" ex Givaudan), 2-ethylhexyl dimethoxybenzylidenedioxoimidazolidinepropionate (see the above-mentioned Japanese patent application laid-open (kokai) No. 101371/1988), (2'-hydroxy-5'-methylphenyl)benzotriazole, methyl anthranylate and the like.

By the way, 4-t-butyl-4-methoxybenzoylmethane and 2-ethylhexyl dimethoxybenzylidenedioxoimidazolidinepropionate which is a benzal hydantoin derivative, both mentioned above, are excellent as a UV-A absorbent. Especially, 2-ethylhexyl dimethoxybenzylidenedioxoimidazolidinepropionate is a derivative of tyrosine, an amino acid, and preferable from the aspect of safety. Further, it has maximum absorption in the vicinity of 344 nm, and is an ultraviolet ray absorbent having a high UV-A absorbability. It has been already marketed under a tradename "Soft Shade DH" (ex Ajinomoto co., Inc.).

These UV absorbents are, as described above, solids which are sparingly soluble both in water and oil, have a poor compatibility with cosmetic compositions, skin medicines for external application or the like, and crystals tend to be precipitated over the course of time. Thus, they have been deemed problematic. Especially, with respect to 2-ethylhexyl dimethoxybenzylidenedioxoimidazolidinepropionate, there have been no oily agents having an excellent dissolving power.

Next, the N-long-chain acyl neutral amino acid ester and the N-long-chain acyl acidic amino acid diester which are the other essential ingredient of the ultraviolet ray-absorbing composition of the present invention will be described.

First, the N-long-chain acyl neutral amino acid ester is exactly the same as the N-long-chain acyl neutral amino acid ester described above with respect to the first invention.

Then, the N-long-chain acyl acidic amino acid diester will be described in detail.

The long-chain acyl group of the N-long-chain acyl acidic amino acid diester of the present invention is the same as the long-chain acyl group of the N-long-chain acyl neutral amino acid ester described above, and preferable examples of the acyl group are the same as those described above.

Further, examples of the acidic amino acid constituting the acidic amino acid moiety include glutamic acid, aspartic acid and the like. Especially preferable is glutamic acid. These amino acids may be either optically active compounds or racemic compounds.

The hydrocarbon group of the alcohol constituting the ester is the same as that of the N-long-chain acyl neutral amino acid ester described earlier, and preferable examples thereof are also the same as those described earlier.

When preferable examples of the N-long-chain acyl acidic amino acid diester of the present invention are represented by a general formula, those represented by Formula (2) below can be mentioned.

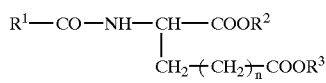

(2)

Wherein
R$^1$ is the same as R$^1$ in Formula (1),
R$^2$ and R$^3$ are, independently from each other, the same as R$^4$ in Formula (1), and
n is an integer of 0 or 1.

The N-long-chain acyl acidic amino acid diester of the present invention can be obtained by, for example, esterifying an N-long-chain acyl acidic amino acid and an alcohol through heat-dehydrocondensation under atmospheric pressure or reduced pressure. Further, it can also be obtained by an azeotropic dehydrocondensation reaction using a solvent such as toluene or the like or by transesterification reaction. The N-long-chain acyl acidic amino acid and the alcohol to be used to obtain the N-long-chain acyl acidic amino acid diester are not necessarily single compounds, and they may be a mixture of N-long-chain acyl acidic amino acids containing different acyl groups and/or acidic amino acids and a mixture of alcohols which are different in the chain length or the like.

Incidentally, the N-long-chain acyl acidic amino acid can be produced by a known method such as the so-called Schotten-Baumann reaction (see Japanese patent publications (kokoku) Nos. 8685/1971, 35058/1973, 38681/1976 and the like) in which a long-chain fatty acid halide is reacted with an amino acid in the presence of a basic catalyst.

Of these N-long-chain acyl amino acid esters, the N-long-chain acyl neutral amino acid ester is more preferable in view of stickiness and solubility.

The simplest embodiment or form of the ultraviolet ray-absorbing composition of the present invention is a composition composed substantially of one or more of the ultraviolet ray absorbents explained above, and one or more of the N-long-chain acyl neutral amino acid esters explained above or/and one or more of the N-long-chain acyl acidic amino acid diesters explained above and it can be put into circulation in as such form.

The preparation of such composition is not particularly limited, nor difficult to do, and the composition can be prepared by an appropiate known method.

The amount of UV absorbent in the composition of this embodiment is usually between 0.01 and 50% by weight, preferably between 0.1 and 20% by weight, and especially preferably between 0.1 and 10% by weight. Further, needless to say, it is advisable that a sparingly-soluble UV absorbent is incorporated in such amount that crystals are not precipitated.

Further, a UV absorbent and an N-long-chain acyl neutral amino acid ester or/and an N-long-chain acyl acidic amino acid diester can be used in the form of a composition of the above-mentioned embodiment, or can be directly used without having been formed into a composition of such embodiment in advance, to prepare cosmetic compositions, skin medicines for external application, plastics, emulsion paints, oil paints, coating agents or the like. The thus-prepared cosmetic compositions and the like are, of course, a kind of the ultraviolet ray-absorbing composition of the present invention. When it is incorporated in cosmetic compositions or skin medicines for external application, the UV absorbent is used in an amount of up to 20% by weight based on the total amount of the final product.

The ultraviolet ray-absorbing composition of the present invention in the form of cosmetic compositions or the like can be prepared by a known method including starting materials, except that a UV absorbent and an N-long-chain acyl neutral amino acid ester or/and an N-long-chain acyl acidic amino acid diester are incorporated into the other starting materials in predetermined amounts.

When an ultraviolet ray-absorbing composition of the present invention is used as a cosmetic composition or skin medicines for external application, it can be one of various cosmetic compositions and skin medicines for external application such as creansing cream, massage cream, cold cream, moisture cream, milky lotion, lotion, hand cream, foundation, lipstick, press powder, eye shadow, hair oil or cream in stick form, hair liquid, setting lotion, haircream, hair lotion, hair mousse, anti-sunburn cream, antisunburn oil, an external pharmaceutical composition and the like. Further, the form thereof is not particularly limited, and any form will do. Examples thereof include an emulsion type, a solution type, a soluble type, a powder dispersion type, a water-oil two-layer type, a water-oil-powder three-layer type and the like.

When an ultraviolet ray-absorbing composition of the present invention is prepared into a cosmetic composition or a skin medicine for external application, some other oily materials can also be incorporated unless the effects of the present invention are impaired. Such oily materials are exactly the same as the other oily materials as described earlier, which can be incorporated in a cosmetic composition of the first invention.

Further, the cosmetic compositions and the skin medicines for external application according to the present invention, can contain one or more of various surfactants unless the effects of the present invention are impaired. Such surfactants are exactly the same as those as described earlier, which can be incorporated into a cosmetic composition of the first invention.

Still further, the cosmetic compositions and the skin medicines for external application according to the present invention can contain, other than those components mentioned above, various additives which are ordinarily used in a cosmetic composition unless the effects of the present invention are impaired. Such various additives are exactly the same as those as described earlier, which can be incorporated into the cosmetic composition of the first invention.

In view of the background concerning the third invention, the inventors have assiduously conducted investigations, and have consequently found that the above-mentioned problems can be solved by using, when an inorganic pigment is incorporated into cosmetic compositions or the like, a specific N-long-chain acyl neutral or acidic amino acid ester along therewith. These findings have led to the completion of the present invention.

Accordingly, the third invention relates to an inorganic pigment composition characterized by containing, as active ingredients, an inorganic pigment and (A) an N-long-chain acyl neutral amino acid ester containing a straight-chain or branched-chain, saturated or unsaturated acyl group having from 6 to 22 carbon atoms, where the hydrocarbon group of the alcohol constituting the ester is a straight-chain or branched-chain, saturated or unsaturated hydrocarbon group having from 1 to 10 carbon atoms or/and (B) an N-long-chain acyl acidic amino acid diester containing a straight-chain or branched-chain, saturated or unsaturated acyl group having from 6 to 22 carbon atoms, where the hydrocarbon group of the alcohol constituting the ester is a straight-chain or branched-chain, saturated or unsaturated hydrocarbon group having from 1 to carbon atoms.

Incidentally, these two types of the esters are less irritative to the skin, and can be an excellent oily material (oily agent) of a cosmetic composition or the like, as has been described.

Now, the third invention will be described in greater detail below.

First, powdery inorganic pigments, one of the ingredients of the inorganic pigment composition of the present invention will be described.

Examples of the inorganic pigment to be used in cosmetic compositions include titanium dioxide, zinc oxide, iron oxide (red iron oxide), iron titanate, γ-iron oxide, yellow iron oxide, loess, black iron oxide, carbon black, lower titanium oxide, mango violet, palto violet, chromium oxide, chromium hydroxide, cobalt titanate, ultramarine, Prussian blue, titanium oxide-coated mica, titanium oxide-coated bismuth oxychloride, titanium oxide-coated talc, colored titanium oxide-coated mica, bismuth oxychloride, fish scale flake, aluminum powder, copper powder, gold powder, mica, talc, kaolin, sericite, white mica, phlogopite, synthetic mica, lepidolite, biotite, lithia mica, vermiculite, calcium carbonate, magnesium carbonate, aluminum silicate, barium silicate, calcium silicate, magnesium silicate, strontium silicate, tungstic acid metal salt, silica, zeolite, barium sulfate, calcined calcium sulfate (calcined gypsum), calcium phosphate, fluorine apatite, hydroxyapatite, ceramic powder, metallic soap (zinc myristate, calcium palmitate, aluminum stearate and the like), boron nitride, photochromic pigment and the like. Further, an inorganic pigment surface-treated with a surface modifier or the like will do. Examples thereof include inorganic pigments coated with Nε-lauroyl lysine, perfluoroalkyl phosphate diethanolamine, sodium metaphosphate, amino acid, acylated collagen, lecitin, metallic soap, acyl amino acid salt, silicone such as methylhydrogen polysiloxane or the like, polyacrylic acid, chitosan, nylon powder, color pigment or the like. Even an inorganic pigment of which the dispesibility has been improved through such surface treatment, the dispersibility can be further improved using the acyl amino acid ester of the present invention. These inorganic pigments may be used either singly or in combination of one or more thereof, depending on the use purpose.

When the inorganic pigments are incorporated into cosmetic compositions, one or more of these pigments are combined, if necessary or desired, and oily material(s), water-soluble material(s), surfactant(s), flavor(s), chemical (s) and the like for cosmetics are added thereto and dispersed therein. The role of the inorganic pigment in cosmetic compositions is great. A color pigment adjusts the color tone of a product, and a white pigment controls the color tone and also the hiding power. An extender pigment adjusts the color tone as a diluent, and also use properties (extensibility, adhesion), a gloss and the like of a product. Further, the extender pigment is also used to maintain the form of the product. A pearlescent pigment gives a product a glaze. Pigments having special functions have been developed relatively recently in order to increase use properties or a makeup effect as well as an ultraviolet ray-scattering effect upon incorporating the same into a product.

The size (particle size) of the powdery inorganic pigment to be contained in the inorganic pigment composition of the present invention is not particularly limited, and a size corresponding to each composition can be determined. The adjustment of the size to an appropriate value is not particularly limited. The adjustment of the size can be conducted before an inorganic pigment is incorporated as an ingredient (in advance) or during the starting materials of a desired composition are added and kneaded to prepare the compositon, as can be seen in production of a color pigment composition. Of course, it is also possible that the size is adjusted to some extent in advance and further adjusted, as required, in kneading the starting materials.

Next, the N-long-chain acyl neutral or acidic amino acid ester which is another essential ingredient of the inorganic pigment composition of the present invention will be described.

Such N-long-chain acyl neutral amino acid ester is exactly the same as the N-long-chain acyl neutral amino acid ester described earlier with respect to the first invention.

When preferable examples of the N-long-chain acyl neutral amino acid ester of the present invention are represented by a general formula, those represented by Formula (1) above can be mentioned.

Further, the N-long-chain acyl acidic amino acid diester is exactly the same as the N-long-chain acyl acidic amino acid diester described earlier with respect to the second invention.

These N-long-chain acyl amino acid esters are less irritative to the skin or the mucous membrane, and are excellent in feelings upon use such as extensibility on, adaptability with, and smoothness to, the skin. Accordingly, these are excellent when used as an oily material for cosmetics in particular. Especially, the N-long-chain acyl neutral amino acid ester is free from unpleasant oily feeling and stickiness peculiar to an oily material, and is excellent in a light feeling such as a clean or dry feeling. Thus, it is better than the N-long-chain acyl acidic amino acid diester when it is used in a cosmetic composition.

The simplest embodiment or mode of the inorganic pigment composition of the present invention is a mixture composed substantially of the powdery inorganic pigment and the N-long-chain acyl neutral amino acid ester or/and the N-long-chain acyl acidic amino acid diester, and it can as such be put into circulation. This is later incorporated into cosmetics, paints or the like as required.

The preparetion of such a mixture is not particularly limited, nor difficult to do. It can be conducted by an appropriate known method. The amount of a powdery inorganic pigment in the mixture of this embodiment is determined according to the intended use. The remainder is the N-long-chain acyl neutral amino acid ester or/and the N-long-chain acyl acidic amino acid diester.

It is also possible to form the inorganic pigment composition of the present invention by coating the N-long-chain acyl amino acid ester on the (particle) surface of the inorganic pigment, instead of preparing such a simple mixture.

The coating method is not particularly limited. The coating can be conducted by, for example, a method in which the N-long-chain acyl amino acid ester of the present invention is dissolved in a solvent such as ethanol or the like, the pigment is then dispersed therein, and the solvent is then distilled off through evaporation. When the coating is conducted to prepare the inorganic pigment composition of the present invention, the amount of the N-long-chain acyl amino acid ester is not particularly limited. It can usually be adjusted to from 1 to 5% by weight based on the inorganic pigment.

Further, the inorganic pigment and the N-long-chain acyl neutral amino acid ester or/and the N-long-chain acyl acidic amino acid diester can be used in the form of a composition of the foregoing mode (mixture and coated), or can be directly incorporated without having been formed into a composition of such mode in advance, to provide cosmetics, paints, ink and the like. The thus-prepared cosmetics and the like are of course a kind of the inorganic pigment composition of the present invention.

The amount of an inorganic pigment in the composition of this embodiment is determined according to the use of the composition. For example, in case of cosmetic compositions, it is ordinarily used in the range of from 0.01 to 90% by weight. The amount of the N-long-chain acyl amino acid ester of the present invention relative to the inorganic pigment is also determined according to the use of the composition. When it is used as a cosmetic compositions, it is usually (inorganic pigment)/(N-long-chain acyl amino acid ester)=100/0.1 to 1/100, and preferably 100/1 to 10/100. When the ratio of the N-long-chain acyl amino acid ester is low, satisfactory dispersibility of the inorganic pigment is not provided sometimes.

The inorganic pigment composition of the present invention in the mode of cosmetics or the like can be prepared by a conventional method including starting materials, except that the inorganic pigment and the N-long-chain acyl neutral amino acid ester or/and the N-long-chain acyl acidic amino acid diester (an embodiment (coating) where the latter is coated onto the particle suraces of the former is naturally included also) are incorporated in predetermined amounts into the other starting materials.

When the inorganic pigment composition of the present invention is used as a cosmetic composition, it can be one of various cosmetic compositions, such as cleansing cream, massage cream, cold cream, moisture cream, milky lotion, lotion, hand cream, foundation, lipstick, press powder, eye shadow, hair oil or cream in stick form, hair liquid, setting lotion, hair cream, hair lotion, hair mousse, anti-sunburn cream, anti-sunburn oil and the like. Further, the form is not particularly limited. Any form will do. Examples thereof include an emulsion form, a solution form, a soluble form, a powder dispersion form, a water-oil two-layer form, a water-oil-powder three-layer form and the like.

When an inorganic pigment composition of the present invention is prepared into a cosmetic composition, some other oily materials can optionally be incorporated unless the effects of the present invention are impaired. Such oily materials are exactly the same as the other oily materials which can be incorporated into a cosmetic composition of the first invention, as has been described earlier.

Further, one or more of various surfactants can also be added to the cosmetic composition according to the present invention unless the effects of the present invention are impaired. Such surfactants are exactly the same as those which can be incorporated into the cosmetic composition of the first invention, as has been described earlier.

Still further, in addition to those components mentioned above, various additives which are ordinarily used in a cosmetic composition can also be added to the cosmetic compositons according to the present invention. Such various additives are exactly the same as those as described earlier, which can be incorporated into the cosmetic composition of the first invention.

BEST MODE FOR CARRYING OUT THE INVENTION

The invention will be illustrated more specifically by referring to Examples including Synthesis Examples, Reference Synthesis Examples, Examination Examples and Formulation Examples of cosmetic compositions. However, the invention is not limited to these Examples.

SYNTHESIS EXAMPLE 1

Synthesis of N-octanoylglycine isopropyl ester

Fifty(50) grams of N-octanoylglycine and 500 ml of isopropanol were charged into a 1,000-milliliter flask, and 1 ml of conc. sulfuric acid was further added thereto as the catalyst. The mixture was heated under reflux for reaction for 8 hours.

After the completion of the reaction, the reaction mixture was allowed to stand to room temperature. After the reaction mixture had got cool, the excess isopropanol was distilled off under reduced pressure. The concentrate was charged into an oil separator, and was, while being maintained at 50° C., neutralized by the addition of approximately 300 ml of an aqueous saturated solution of sodium hydrogencarbonate. The resulting oily phase was separated. Further, the oily phase was washed with water, and then dried under reduced pressure to obtain 39 g (64% yield) of the captioned compound as a white solid.

ESI (Electrospray Ionization)-MS: 244 (M+H)+.

IR (KBr): 2900 $cm^{-1}$ (C—H), 1710 $cm^{-1}$ (ester), 1640 $cm^{-1}$ (amide).

SYNTHESIS EXAMPLE 2

Synthesis of N-octanoyl-N-methyl-β-alanine isopropyl ester

Fifty-seven(57) grams of N-octanoyl-N-methyl-β-alanine and 500 ml of isopropanol were charged into a 1,000-milliliter flask, and 1 ml of conc. sulfuric acid was further added thereto as the catalyst. The mixture was heated under reflux reaction for 8 hours.

After the completion of the reaction, the reaction mixture was allowed to stand to room temperature. Then, the excess isopropanol was distilled off under reduced pressure. The concentrate was neutralized by the addition of approximately 300 ml of an aqueous saturated solution of sodium hydrogencarbonate. The resulting oily phase was separated. Further, the oily phase was washed with water, and then dried under reduced pressure to obtain 57 g (84% yield) of the captioned compound as a transparent solid.

IR (neat): 2950 cm$^{-1}$ (C—H), 1710 cm$^{-1}$ (ester), 1640 cm$^{-1}$ (amide).

SYNTHESIS EXAMPLE 3

Synthesis of N-octanoyl-β-alanine Octyl Ester

Fifty-seven(57) grams of N-octanoyl-β-alanine and 36 g of octanol, and 500 ml of toluene as the solvent were charged into a 1,000-milliliter flask, and 2 g of p-toluenesulfonic acid monohydrate was further added thereto as the catalyst. The mixture heated under reflux for reaction for 8 hours.

After the completion of the reaction, the reaction mixture was allowed to stand to room temperature. After the reaction mixture had got cool, it was neutralized by the addition of approximately 500 ml of an aqueous saturated solution of sodium hydrogencarbonate. The resulting organic phase was separated. The organic phase was washed with water, and the excess toluene was distilled off under reduced pressure. The residue was further recrystallized form hexane and dried under reduced pressure to obtain 50 g (57% yield) of the captioned compound as a solid.

IR (KBr): 2900 cm$^{-1}$ (C—H), 1730 cm$^{-1}$ (ester), 1640 cm$^{-1}$ (amide).

SYNTHESIS EXAMPLE 4

Synthesis of N-lauroyl-γ-aminobutyric acid octyl ester

Fifty-seven(47) grams of N-lauroyl-γ-aminobutyric acid and 24 g of octanol, and 500 ml of toluene were charged into a 1,000-milliliter flask, and 2 g of p-toluenesulfonic acid monohydrate was further added thereto as the catalyst. The mixture was heated under reflux for reaction for 8 hours.

After the completion of the reaction, the reaction mixture was allowed to stand to room temperature. After the reaction mixture had got cool, it was neutralized by the addition of approximately 500 ml of an aqueous saturated solution of sodium hydrogencarbonate. The resulting oily phase was separated. The oily phase was washed with water, and the excess toluene was distilled off under reduced pressure. The residue was further recrystallization from hexane and dried under reduced pressure to obtain 42 g (63% yield) of the captioned compound as a solid.

IR (KBr): 2900 cm$^{-1}$ (C—H), 1730 cm$^{-1}$ (ester), 1640 cm$^{-1}$ (amide).

SYNTHESIS EXAMPLE 5

Synthesis of N-coconut oil fatty acid acyl alanine isopropyl ester

One hundred(100) grams of N-coconut oil fatty acid acyl alanine (composition of the acyl groups (weight ratio); capryl group: 1.3%, caproyl group: 9.4%, lauroyl group: 58.7%, myristoyl group: 18.5%, and palmitoyl group: 2.1%) and 750 ml of isopropanol were charged into a 1,000-milliliter flask. Further, 2 ml of conc. sulfuric acid were added as the catalyst. The mixture was heated under reflux for reaction for 20 hours.

After the completion of the reaction, the reaction mixture was allowed to stand to room temperature. After the reaction mixture had got cool, the excess isopropanol was distilled off under reduced pressure. The concentrate was neutralized by the addition of approximately 500 ml of an aqueous saturated solution of sodium hydrogencarbonate. The resulting oily phase was washed with water, and dried under reduced pressure to obtain 82 g (71% yield) of the captioned compound as a clear liquid.

ESI-MS: 286, 314, 342 (M+H)+.

IR (neat): 2950 cm$^{-1}$ (C—H), 1725 cm$^{-1}$ (ester), 1600 cm$^{-1}$ (amide).

SYNTHESIS EXAMPLE 6

Synthesis of N-myristoyl-γ-aminobutyric acid isopropyl ester

Forty(40) grams of N-myristoyl-γ-aminobutyric acid and 500 ml of isopropanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess isopropanol was distilled off under reduced pressure. The residue was dissolved in 300 ml of diethyl ether and neutralized by the addition of approximately 300 ml of an aqueous saturated solution of sodium hydrogencarbonate. The resulting organic phase was washed with water, and dried over approximately 5 g of anhydrous magnesium sulfate, and the anhydrous magnesium sulfate was then filtered off. The ether was distilled away from the mother liquor. The residue was recrystallized from ethanol and dried under reduced pressure to obtain 25 g (56% yield) of the captioned compound as a solid.

IR (KBr): 2940 cm$^{-1}$ (C—H), 1730 cm$^{-1}$ (ester), 1610 cm$^{-1}$ (amide).

SYNTHESIS EXAMPLE 7

Synthesis of N-myristoyl glycine octyl ester

Thirty-six(36) grams of N-myristoyl glycine and 16 g of actanol, and 300 ml of toluene were charged into a 500-milliliter flask. Further, 1 g of p-toluenesulfonic acid monohydrate was added as the catalyst. The mixture was heated under reflux for reaction for 10 hours.

After the completion of the reaction, the reaction mixture was allowed to stand to room temperature. After the reaction mixture had got cool, it was neutralized by the addition of approximately 300 ml of an aqueous saturated solution of sodium hydrogencarbonate. The resulting organic phase was separated and washed with water. The excess toluene was distilled away under reduced pressure. The residue was recrystallized from hexane and dried under reduced pressure to obtain 27 g (66% yield) of the captioned compound as a solid.

IR (KBr): 2950 cm$^{-1}$ (C—H), 1725 cm$^{-1}$ (ester), 1600 cm$^{-1}$ (amide).

SYNTHESIS EXAMPLE 8

Synthesis of N-stearoyl alanine octyl ester

Forty(40) grams of N-stearoyl alanine and 16 g of octanol, and 400 ml of toluene were charged into a 500-milliliter flask. Further, 1 g of p-toluenesulfonic acid monohydrate was added as the catalyst. The mixture was heated under reflux for reaction for 6 hours.

After the completion of the reaction, the reaction mixture was allowed to stand to room temperature. After the reaction mixture had got cool, it was neutralized by the addition of approximately 500 ml of an aqueous saturated solution of sodium hydrogencarbonate. The resulting organic phase was separated and washed with water, and the excess toluene was distilled away under reduced pressure. The residue was recrystallized from hexane and dried under reduced pressure to obtain 34 g (65% yield) of the captioned compound as a solid.

IR (KBr): 2930 cm$^{-1}$ (C—H), 1730 cm$^{-1}$ (ester), 1630 cm$^{-1}$ (amide).

SYNTHESIS EXAMPLE 9

Synthesis of N-lauroyl alanine ethyl ester

One hundred(100) grams of N-lauroyl alanine and 750 ml of ethanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess ethanol was distilled off under reduced pressure. The concentrate was charged into an oil separator and was, while being maintained at 50° C., neutralized by the addition of approximately 300 ml of an aqueous saturated solution of sodium hydrogencarbonate. The resulting oily phase was separated, washed with water, and allowed to stand to room temperature, followed by recrystallizing from ethanol. The crystals were dried under reduced pressure to obtain 81 g (73% yield) of the captioned compound as a solid.

ESI-MS: 300 (M+H)+.

IR (KBr): 2930 cm$^{-1}$ (C—H), 1730 cm$^{-1}$ (ester), 1630 cm$^{-1}$ (amide).

SYNTHESIS EXAMPLE 10

Synthesis of N-lauroyl alanine t-butyl ester

One hundred(100) grams of N-lauroyl alanine and 750 ml of t-butanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess t-butanol was distilled off under reduced pressure. The concentrate was charged into an oil setarator and was, while being maintained at 50° C., neutralized by the addition of approximately 300 ml of an aqueous saturated solution of sodium hydrogencarbonate. The resulting oily phase was separated, washed with water, and allowed to stand to room temperature, followed by recrystallizing from ethanol. The crystals were dried under reduced pressure to obtain 80 g (70% yield) of the captioned compound as a solid.

ESI-MS: 328 (M+H)+.

IR (KBr): 2910 cm$^{-1}$ (C—H), 1720 cm$^{-1}$ (ester), 1620 cm$^{-1}$ (amide).

SYNTHESIS EXAMPLE 11

Synthesis of N-lauroyl alanine propyl ester

One hundred(100) grams of N-lauroyl alanine and 750 ml of propanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess propanol was distilled off under reduced pressure. The concentrate was charged into an oil separator and was, while being maintained at 50° C., neutralized by the addition of approximately 300 ml of an aqueous saturated solution of sodium hydrogencarbonate. The resulting oily phase was sepatated, washed with water, and allowed to stand to room temperature, followed by recrystallizing from ethanol. The crystals were dried under reduced pressure to obtain 84 g (73% yield) of the captioned compound as a solid.

ESI-MS: 314 (M+H)+.

IR (KBr): 2910 cm$^{-1}$ (C—H), 1710 cm$^{-1}$ (ester), 1630 cm$^{-1}$ (amide).

SYNTHESIS EXAMPLE 12

Synthesis of N-coconut oil fatty acid acyl sarcosine isopropyl ester

One hundred(100) grams of N-coconut oil fatty acid acyl sarcosine and 750 ml of isopropanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess isopropanol was distilled off under reduced pressure. The concentrate was neutralized by the addition of approximately 500 ml of an aqueous saturated solution of sodium hydrogencarbonate. The resulting oily phase was washed with water, and dried to obtain 90 g (78% yield) of the captioned compound as a liquid.

IR (neat): 2950 cm$^{-1}$ (C—H), 1720 cm$^{-1}$ (ester), 1630 cm$^{-1}$ (amide).

SYNTHESIS EXAMPLE 13

Synthesis of N-coconut oil fatty acid acyl-N-methyl-β-alanine isopropyl ester

Eighty(80) grams of N-coconut oil fatty acid acyl-N-methyl-β-alanine and 750 ml of isopropanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess isopropanol was distilled off under reduced pressure. The concentrate was neutralized by the addition of approximately 500 ml of an aqueous saturated solution of sodium hydrogencarbonate. The resulting oily phase was washed with water, and dried under reduced pressure to obtain 67 g (73% yield) of the captioned compound as a liquid.

IR (neat): 2950 cm$^{-1}$ (C—H), 1720 cm$^{-1}$ (ester), 1640 cm$^{-1}$ (amide).

SYNTHESIS EXAMPLE 14

Synthesis of N-laurolysarcosine isopropyl ester

One hundred(100) grams of N-lauroylsarcosine and 750 ml of isopropanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. After the reaction mixture had got cool, the excess isopropanol was distilled off under reduced pressure. The concentrate was neutralized by the addition of approximately 500 ml of an aqueous saturated solution of sodium hydrogencarbonate. The resulting oily phase was washed with water, and dried under reduced pressure to obtain 98 g (85% yield) of the captioned compound as a colorless clear liquid.

ESI-MS: 314 (M+H)+.

IR (neat): 2940 cm$^{-1}$ (C—H), 1730 cm$^{-1}$ (ester), 1650 cm$^{-1}$ (amide).

SYNTHESIS EXAMPLE 15

Synthesis of N-lauroyl-N-methyl-β-alanine isopropyl ester

One hundred grams(100) of N-lauroyl-N-methyl-β-alanine and 750 ml of isopropanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. After the reaction mixture had got cool, the excess isopropanol was distilled off under reduced pressure. The concentrate was neutralized by the addition of approximately 500 ml of an aqueous saturated solution of sodium hydrogencarbonate. The resulting oily phase was washed with water, and dried under reduced pressure to obtain 80 g (70% yield) of the captioned compound as a clear liquid.

ESI-MS: 828 (M+H)+.

IR (neat): 2950 cm$^{-1}$ (C—H), 1720 cm$^{-1}$ (ester), 1640 cm$^{-1}$ (amide).

SYNTHESIS EXAMPLE 16

Synthesis of N-lauroylglycine isopropyl ester

Sixty(60) grams of N-lauroylglycine and 750 ml of isopropanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess isopropanol was distilled off under reduced pressure. The residue was dissolved in 300 ml diethyl ether and neutralized with approximately 300 ml of an aqueous saturated solution of sodium hydrogencarbonate. The resulting organic phase was washed with water, and dried over approximately 20 g of anhydrous magnesium sulfate. The anhydrous magnesium sulfate was then filtered off. The ether was distilled away from the mother liquor. The residue was recrystallized from ethanol and dried under reduced pressure to obtain 45 g (64% yield) of the captioned compound as a solid.

ESI-MS: 300 (M+H)+.

IR (KBr): 2920 cm$^{-1}$ (C—H), 1720 cm$^{-1}$ (ester), 1620 cm$^{-1}$ (amide).

SYNTHESIS EXAMPLE 17

Synthesis of N-lauroyl alanine isopropyl ester

One hundred(100) grams of N-lauroyl alanine and 750 ml of isopropanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess isopropanol was distilled off under reduced pressure. The concentrate was charged into an oil separator and was, while being maintained at 50° C., neutralized by the addition of approximately 300 ml of an aqueous saturated solution of sodium hydrogencarbonate. The resulting oily phase was separated washed with water, and dried under reduced pressure to obtain 83 g (73% yield) of the captioned compound as a solid.

ESI-MS: 314 (M+H)+.

IR (KBr): 2910 cm$^{-1}$ (C—H), 1715 cm$^{-1}$ (ester), 1630 cm$^{-1}$ (amide).

SYNTHESIS EXAMPLE 18

Synthesis of N-lauroylsarcosine propyl ester

Sixty-one(61) grams of N-lauroylsarcosine (ex. Kawaken Fine Chemicals Co., Ltd.) and 200 ml of 1-propanol were charged into a 500-milliliter flask. Further, 1.45 g of conc. sulfuric acid were added as the catalyst. The mixture was heated under reflux for reaction for 7 hours.

After the comfpletion of the reaction, the reaction mixture was allowed to stand to room temperature. After the reaction mixture had got cool, the excess 1-propanol was distilled off under reduced pressure. The concentrate was neutralized with 76 g of an aqueous 3% solution of sodium hydroxide. The resulting oily phase was washed with water, and dried under reduced pressure to obtain 48 g (68% yield) of the captioned compound as a colorless clear liquid.

ESI-MS: 314 (M+H)+.

IR (neat): 2925 cm$^{-1}$ (C—H), 1750 cm$^{-1}$ (ester), 1650 cm$^{-1}$ (amide).

SYNTHESIS EXAMPLE 19

Synthesis of N-lauroylsarcosine butyl ester

One hundred and thirty-five point five(135.5) grams of N-lauroylsarcosine (ex. Kawaken Fine Chemicals Co., Ltd.) and 200 ml of 1-butanol were charged into a 500-milliliter flask. Further, 4.99 g of conc. sulfuric acid were added as the catalyst. The mixture was heated under reflux for reaction for 6 hours.

After the completion of the reaction, the reaction mixture was allowed to stand to room temperature. After the reaction mixture had got cool, the excess 1-butanol was distilled off under reduced pressure. The concentrate was neutralized with 162 g of an aqueous 3% solution of sodium hydroxide. The resulting oily phase was washed with water, and dried under reduced pressure to obtain 114 g (70% yield) of the captioned compound as a colorlessclear liquid. The acid value of the product was 0.6.

SYNTHESIS EXAMPLE 20

Synthesis of N-lauroylleucine isopropyl ester

Forty-nine(49) grams of N-lauroylleucine and 95 g of isopropanol were charged into a 500-milliliter flask. Further, 1.61 g of conc. sulfuric acid were added as the catalyst. The mixture was heated under reflux for reaction for 2 hours. After the completion of the reaction, the excess isopropanol was distilled off under reduced pressure. The concentrate was added with 94 g of isopropanol, and the mixture was heated under reflux for reaction for 5 hours.

After the completion of the reaction the excess isopropanol was distilled away under reduced pressure. The concentrate was allowed to stand to room temperature. After the concentrate had got cool, it was neutralized with 87 g of an aqueous 3% solution of sodium hydroxide. The resulting oily phase was washed with water, and dried under reduced pressure to obtain 44 g (77% yield) of the captioned compound as a light-yellow, clear liquid.

ESI-MS: 356 (M+H)+.

IR (neat): 2925 cm$^{-1}$ (C—H), 1740 cm$^{-1}$ (ester), 1650 cm$^{-1}$ (amide).

SYNTHESIS EXAMPLE 21

Synthesis of N-lauroylvaline isopropyl ester

Forty-nine(49) grams of N-lauroylvaline and 197 g of isopropanol were charged into a 500-milliliter flask. Further, 1.61 g of conc. sulfuric acid were added as the catalyst. The mixture was heated under reflux for reaction for 6 hours.

After the completion of the reaction, the excess isopropanol was distilled off under reduced pressure. After the concentrate had got cool, it was neutralized with 77 g of an aqueous 3% solution of sodium hydroxide. The resulting oily phase was washed with water, and dried under reduced pressure to obtain 41 g (73% yield) of the captioned compound as a paste or solid. The acid value of the product was 1.5.

ESI-MS: 342 (M+H)+.

IR (neat): 2925 cm$^{-1}$ (C—H), 1720 cm$^{-1}$ (ester), 1640 cm$^{-1}$ (amide).

SYNTHESIS EXAMPLE 22

Synthesis of N-coconut oil fatty acid acyl leucine isopropyl ester

Forty-five(45) grams of N-coconut oil fatty acid acyl leucine and 140 g of isopropanol were charged into a 500-milliliter flask. Further, 2.86 g of conc. sulfuric acid were added as the catalyst. The mixture was heated under reflux for reaction for 2 hours. After the completion of the reaction, the excess isopropanol was distilled off under reduced pressure. The concentrate was added with 90 g of isopropanol, and the mixture was heated under reflux for reaction for 1 hour.

After the completion of the reaction, the excess isopropanol was distilled away under reduced pressure. The concentrate was allowed to stand to room temperature. After the concentrate had got cool, it was neutralized with 184 g of an aqueous 3% solution of sodium hydroxide. The resulting oily phase was washed with water, and dried under reduced pressure to obtain 38 g (74% yield) of the captioned compound as a light-yellow, clear liquid. The acid value of the product was 1.8.

ESI-MS: 356 (M+H)+.

IR (neat): 2930 cm$^{-1}$ (C—H), 1740 cm$^{-1}$ (ester), 1645 cm$^{-1}$ (amide).

REFERENCE SYNTHESIS EXAMPLE 1

Synthesis of N-lauroylsarcosine isostearyl ester

Ten(10) grams of N-lauroylsarcosine and 8.6 g of isostearyl alcohol were charged into a 200-milliliter flask. Further, 0.5 g of p-toluenesulfonic acid monohydrate were added as the catalyst. The mixture was maintained at 130° C. for 3 hours.

After the completion of the reaction, the reaction mixture was allowed to stand to room temperature. After the reaction mixture had got cool, it was added with approximately 200 ml of an aqueous saturated solution of sodium hydrogencarbonate. The resulting oily phase was washed with water, and dried enough by adding anhydrous magnesium sulfate. The anhydrous magnesium sulfate was then filtered off to obtain 16 g (86% yield) of the captioned compound as a liquid.

IR (neat): 2920 m$^{-1}$ (C—H), 1720 cm$^{-1}$ (ester), 1650 cm$^{-1}$ (amide).

REFERENCE SYNTHESIS EXAMPLE 2

Synthesis of N-lauroylsarcosine octyl dodecyl ester

Ten(10) grams of N-lauroylsarcosine and 9.5 g of octyldodecanol were charged into a 200-milliliter flask. Further, 0.5 g of p-toluenesulfonic acid were added as the catalyst. The mixture was maintained at 130° C. for reaction for 3 hours.

After the completion of the reaction, the reaction mixture was allowed to stand to room temperature. After the reaction mixture had got cool, it was added with approximately 200 ml of an aqueous saturated solution of sodium hydrogencarbonate. The resulting oily phase was washed with water, and dried enough by adding 5 g of anhydrous magnesium sulfate. The anhydrous magnesium sulfate was then filtered off to obtain 17 g (87% yield) of the captioned compound as a liquid.

IR (neat): 2930 cm$^{-1}$ (C—H), 1720 cm$^{-1}$ (ester), 1640 cm$^{-1}$ (amide).

REFERENCE SYNTHESIS EXAMPLE 3

Synthesis of N-lauroyl alanine octyldodecyl ester

Ten(10) grams of N-lauroyl alanine and 9.5 g of octyldodecanol were charged into a 200-milliliter flask. Further, 0.5 g of p-toluenesulfonic acid were added as the catalyst. The mixture was maintained at 130° C. for reaction for 3 hours.

After the completion of the reaction, the reaction mixture was allowed to stand to room temperature. After the reaction mixture had got cool, it was added with approximately 200 ml of an aqueous saturated solution of sodium hydrogencarbonate. The resulting oily phase was washed with water, and dried enough by adding 5 g of anhydrous magnesium sulfate. The anhydrous magnesium sulfate was then filtered off to obtain 16 g (82% yield) of the captioned compound as a liquid.

IR (neat): 2940 cm$^{-1}$ (C—H), 1730 cm$^{-1}$ (ester), 1650 cm$^{-1}$ (amide).

EXAMINATION EXAMPLE 1

With respect to the feeling of the N-long-chain acyl neutral amino acid esters obtained in Synthesis Examples and Reference Synthesis Examples, the organoleptic evaluation was conducted by five panelists. Each panelist coated an appropriate amount of each oily material on the back of their hand. The organoleptic evaluation was conducted according to the following evaluation standard. That is, the oily agent which was liquid was used as such in the evaluation. The solid agent was once melted by being heated at 45° C., and was then decreased in temperature to form a liquid. The resulting liquid was used in the evaluation.

In the evaluation, with respect to the feeling of each oily agent, it was measured which feeling it had, a light feeling such as "dry" or "clean", or a heavy feeling such as "wet" or "sticky". The results of the evaluation are shown in Table 1 below.

TABLE 1

| | Oily materials used | Light feeling | | Heavy feeling | |
| --- | --- | --- | --- | --- | --- |
| | | dry | clean | wet | sticky |
| Comparative Formulation Example 1 | N-laurolylsarcosine isostearyl ester (Reference Synthesis Example 1) | | 1 | 2 | 2 |
| Comparative Formulation Example 2 | N-lauroylsarcosine octyldodecyl ester (Reference Synthesis Example 2) | | | 2 | 3 |
| Comparative Formulation Example 3 | N-lauroylalanine octyldodecyl ester (Reference Synthesis Example 3) | | | 1 | 4 |
| Formulation Example 1 | N-lauroylsarcosine isopropyl ester (Synthesis Example 14) | 4 | 1 | | |
| Formulation Example 2 | N-lauroyl-N-methyl-β-alanine isopropyl ester (Synthesis Example 15) | 2 | 2 | 1 | |
| Formulation Example 3 | N-lauroylalanine ethyl ester (Synthesis Example 9) | 1 | 4 | | |
| Formulation Example 4 | N-lauroylalanine propyl ester (Synthesis Example 11) | | 5 | | |
| Formulation Example 5 | N-lauroylalanine isopropyl ester (Synthesis Example 17) | 1 | 4 | | |
| Formulation Example 6 | N-lauroylalanine-t-butyl ester (Synthesis Example 10) | | 4 | 1 | |
| Formulation Example 7 | N-coconut oil fatty acid acylalanine isopropyl ester (Synthesis Example 5) | | 5 | | |
| Formulation Example 8 | N-octanoylglycine isopropyl ester (Synthesis Example 1) | 1 | 4 | | |

*Numerals in the table indicate each feeling and the number of persons who evaluated.

Table 1 reveals that the oily materials in Formulation Examples are excellent in the clean or dry feeling.

EXAMINATION EXAMPLE 2

A milky lotion containing each of the oily materials was prepared according to the recipe shown in Table 2 below. Five panelists coated an appropriate amount of each of the milky lotions on the back of their hand, and the organoleptic evaluation was conducted on the basis of the following evaluation standard with respect to clean feeling, extensibility, smoothness and adaptability.

That is, an average value in the evaluation of each panelist based on the evaluation standard was calculated. When the average value was between 1.0 and 2.0, it was rated as very good (∘∘); when the averate value was at least 0.5 and less than 1.0, it was rated as good (∘); and when the average value was at least −1.0 and less than 0.5, it was rated as bad (Δ). The results are shown in Table 3 below.

<Evaluation Standard>

2: very good, 1: good, 0: common (blank), and −1: bad, in which the evaluation score when using liquid paraffin as the oily material was 0 (blank).

TABLE 2

| Recipe of a milky lotion | |
| --- | --- |
| (1) Oily phase | |
| oily material in each of Synthesis Examples or Reference Synthesis Examples | 5.0 |
| liquid paraffin | 9.5 |
| propylene glycol monostearate | 0.3 |
| behenyl alcohol | 0.5 |
| glycerol monostearate | 1.0 |
| POE (10) monostearate | 1.0 |
| butyl para-hydroxybenzoate | 0.1 |
| (2) Aqueous phase | |
| carboxyvinyl polymer (aqueous 1% solution) | 30.0 |
| propylene glycol | 5.0 |
| methyl para-hydroxybenzoate | 0.1 |
| aqueous sodium hydroxide solution (aqueous 10% solution) | (pH adjustment) |
| purified water | balance |
| Total | 100.0 |

The ratio of each component is % by weight. The pH was adjusted to 6.5 with aqueous sodium hydroxide solution.

TABLE 3

| | Oily material used | Clean feeling | Smoothness | Extensibility | Adaptability |
| --- | --- | --- | --- | --- | --- |
| Comparative Formulation Example 4 | isopropyl myristate | ∘ | Δ | Δ | Δ |
| Comparative Formulation Example 5 | N-lauoylalanine octyldodecyl ester (Reference Synthesis Example 3) | Δ | Δ | Δ | Δ |

TABLE 3-continued

| | Oily material used | Clean feeling | Smoothness | Extensibility | Adaptability |
|---|---|---|---|---|---|
| Formulation Example 9 | N-lauroylsarcosine isopropyl ester (Synthesis Example 14) | ⊙⊙ | ⊙⊙ | ⊙⊙ | ⊙⊙ |
| Formulation Example 10 | N-lauroylalanine isopropyl ester (Synthesis Example 17) | ⊙⊙ | ⊙ | ⊙⊙ | ⊙⊙ |

Table 3 reveals that all the Formulation Examples are excellent in the clean feeling, the extensibility, the smoothness and the adaptability in comparison with Comparative Formulation Examples.

EXAMINATION EXAMPLE 3

Five panelists evaluated oily materials when applied to the hair. A 0.05 weight % ethanol solution of each of the oily materials was prepared. The hair of one and the same person was used. The hair with a fixed size and weight (2.5 g) was prepared. Incidentally, before the evaluation, the hair was washed with approximately 1,000 ml of an aqueous 1 weight % sodium lauryl sulfate solution (40° C.), rinsed with warm water of 40° C., and then dried well. This hair was dipped in the ethanol solution for 2 minutes, and redried well.

The conditioning property (good feeling) of the thus-treated hair was evaluated. That is, an average value in the evaluation of each panelist based on the following evaluation standard, as in Examination Example 2, was calculated. When the average value was between 1.0 and 2.0, it was rated as very good (⊙⊙); when the average was at least 0.5 and less than 1.0, it was rated as good (⊙); and when the average value was at least −1.0 and less than 0.5, it was rated as bad (Δ).

The results are shown in Table 4 below.

TABLE 4

| | Oily material used | Conditioning property |
|---|---|---|
| Comparative Formulation Example 6 | isopropyl myristate | Δ |
| Comparative Formulation Example 7 | N-lauroylalanine octyldodecyl ester (Reference Synthesis Example 3) | Δ |
| Formulation Example 11 | N-lauroylsarcosine isopropyl ester (Synthesis Example 14) | ⊙ |
| Formulation Example 12 | N-lauroylalanine isopropyl ester (Synthesis Example 17) | ⊙⊙ |
| Formulation Example 13 | N-coconut oil fatty acid acyl alanine isopropyl ester (Synthesis Example 5) | ⊙⊙ |
| Formulation Example 14 | N-myristoylglycine octyl ester (Synthesis Example 7) | ⊙ |
| Formulation Example 15 | N-stearoylalanine octyl ester (Synthesis Example 8) | ⊙ |

Table 4 reveals that all the Formulation Examples are excellent in the hair conditioning property in comparison with Comparative Formulation Examples.

FORMULATION EXAMPLE 16

Lotion

A lotion having the composition shown in Table 5 below was prepared in a usual manner. That is, the components under Component 1 and 2 were dissolved, respectively, and the components under Component 1 was then mixed with those under Component 2.

TABLE 5

| Lotion | |
|---|---|
| (Component 1) | |
| propylene glycol | 6.0 |
| glycerol | 5.0 |
| polyethylene glycol 4000 | 3.0 |
| purified water | balance |
| (Component 2) | |
| N-coconut oil fatty acid acylsarcosine isopropyl ester | 0.5 |
| POE (20) sorbitan monolauric acid ester | 1.5 |
| POE (5) oleyl alcohol ether | 0.3 |
| ethanol | 10.0 |
| flavor | suitable amount |
| antiseptic | suitable amount |
| Total | 100(%) |

POE = polyoxyethylene

FORMULATION EXAMPLE 17

Emollient Lotion

An emollient lotion having the composition shown in Table 6 below was prepared as follows. That is, the components under Components 1 and 3 were dissolved, respectively. The components under Component 3 were added to the components under Component 1, and these were mixed and emulsified. To this were added the components under Component 2, and they were emulsified using a homomixer to obtain a product.

TABLE 6

| Emollient lotion | |
|---|---|
| (Component 1) | |
| cetyl alcohol | 2.0 |
| bees wax | 0.5 |
| vaseline | 2.0 |
| N-octanoyl-N-methyl-β-alanine isopropyl ester | 6.0 |
| dimethyl polysiloxane | 2.0 |
| glycerol monostearate | 1.0 |
| POE (10) monooleic acid ester | 1.0 |
| (Component 2) | |
| ethanol | 5.0 |
| Quince Seed extract (aqueous 20% solution) | 20.0 |
| (Component 3) | |
| flavor | suitable amount |
| antiseptic | suitable amount |
| purified water | balance |
| Total | 100(%) |

FORMULATION EXAMPLE 18

W/O Type Milky Lotion

A W/O type milky lotion having the composition shown in Table 7 below was prepared in an ordinary method.

TABLE 7

| W/O type milky lotion | |
| --- | --- |
| (Oily phase) | |
| stearyl alcohol | 6.0 |
| stearic acid | 2.0 |
| hydrous lanoline | 4.0 |
| N-octanoylglycine isopropyl ester | 2.0 |
| liquid paraffin | 7.0 |
| octyldodecanol | 10.0 |
| POE (25)cetyl alcohol ester | 3.0 |
| glycerol monostearate | 2.0 |
| (Aqueous phase) | |
| 1,3-butylene glycol | 6.0 |
| polyethylene glycol | 4.0 |
| antiseptic | 0.2 |
| flavor | suitable amount |
| antioxidant | suitable amount |
| purified water | balance |
| Total | 100(%) |

FORMULATION EXAMPLE 19

O/W Type Cream

An O/W type cream having the composition shown in Table 8 below was prepared as follows. That is, an oily phase was heated to 80° C., and an aqueous phase to 50° C. While the oily phase was stirred, the aqueous phase was gradually added thereto for emulsification.

TABLE 8

| O/W type cream | |
| --- | --- |
| (Oily phase) | |
| di(choresteryl, octyldodecyl) N-lauroylglutamate | 2.5 |
| N-2-ethylhexanoylsarcosine isopropyl ester | 9.5 |
| glycerol trioctanoate | 2.5 |
| propylene glycol monostearate | 5.0 |
| dimethyl silicone oil | 5.0 |
| behenyl alcohol | 0.5 |
| glycerol monostearate | 1.0 |
| POE (10) monostearate | 3.0 |
| (Aqueous phase) | |
| antiseptic | 0.2 |
| xanthane gum | 0.05 |
| 1,3-butylene glycol | 5.0 |
| glycine | 1.0 |
| aqueous sodium hydroxide solution (10%) | suitable amount |
| flavor | suitable amount |
| purified water | balance |
| Total | 100(%) |

FORMULATION EXAMPLE 20

Milky Lotion

A milky lotion having the composition shown in Table 9 below was prepared as follows. That is, first, the components under Component 1, those under Component 2 and those under Component 3 were heated to 60° C., respectively. The components under Component 1 were, with stirring, added gradually with the components under Component 2, then with the components under Component 3 and cooled to 30° C.

TABLE 9

| Milky lotion | |
| --- | --- |
| (Component 1) | |
| 1,3-butylene glycol | 1.2 |
| POE(10)POP(20)2-tetradecyl diether | 2.0 |
| POE(5)oleic acid ester | 4.0 |
| (Component 2) | |
| liquid paraffin | 15.0 |
| N-lauroylsarcosine isopropyl ester | 3.0 |
| N-lauroylglycine isopropyl ester | 2.0 |
| (Component 3) | |
| flavor | suitable amount |
| antiseptic | suitable amount |
| purified water | balance |
| Total | 100(%) |

POP = Polyoxypropylene (hereinafter, the same)

FORMULATION EXAMPLE 21

Emollient Cream

An emollient cream having the composition shown in Table 10 below was prepared as follows. First, the components under Component 2 and the components under Component 3 were heated to 50° C., respectively, and the components under Component 3 were gradually added to the components under Component 2 to obtain a mixture. The mixture was uniformly dispersed in a melted mixture obtained by heating the components under Component 1 to 70° C. Further, a product obtained by heating the components under Component 4 to 70° C. was added to the dispersion while being stirred well. The mixture was emulsified using a homomixer to obtain a product.

TABLE 10

| Emollient cream | |
| --- | --- |
| (Component 1) | |
| liquid paraffin | 25.0 |
| academian nut oil | 3.0 |
| N-lauroylglycine isopropyl ester | 2.0 |
| microcrystalline wax | 2.0 |
| vaseline | 5.0 |
| (Component 2) | |
| diglycerol monooleate | 5.0 |
| diglycerol monostearate | 1.0 |
| tocopherol acetate | 0.2 |
| (Component 3) | |
| sodium glutamate | 1.6 |
| serine | 0.4 |
| purified water | 13.0 |
| (Component 4) | |
| propylene glycol | 3.0 |
| antiseptic | suitable amount |
| flavor | suitable amount |
| purified water | balance |
| Total | 100(%) |

FORMULATION EXAMPLE 22

Ultraviolet Ray-inhibiting Essence

An ultraviolet ray-inhibiting essence having the composition shown in Table 11 below was prepared as follows. That is, the wetting agent and the triethanolamine were heat-dissolved in the purified water at 70° C. The oil content was heat-dissolved at 70° C. Then, the surfactant, the ultraviolet absorbent, the antiseptic and the flavor were dissolved therein in this order, and these were uniformly dissolved at 70° C. using a homomixer.

TABLE 11

Ultraviolet-inhibiting essence

| | |
|---|---|
| (Component 1) | |
| stearic acid | 3.0 |
| cetanol | 1.0 |
| lanoline | 3.0 |
| N-lauroyl-t-butyl ester | 2.0 |
| 2-ethylhexyl stearate | 6.0 |
| (Component 2) | |
| 1,3-butylene glycol | 6.0 |
| (Component 3) | |
| POE cetyl alcohol ether | 2.0 |
| glycerol monostearate | 1.0 |
| triethanolamine | 1.0 |
| (Component 4) | |
| 2-hydroxy-4-methoxybenzophenone | 4.0 |
| 4-t-butyl-4'-methoxybenzoylmethane | 4.0 |
| 2-ethylhexyl dimethoxybenzylidenedioxoimidazolidinepropionate | 2.0 |
| (Component 5) | |
| flavor | suitable amount |
| antiseptic | suitable amount |
| purified water | balance |
| Total | 100(%) |

FORMULATION EXAMPLE 23

Suntan Oil

A suntan oil having the composition shown in Table 12 below was prepared in an ordinary manner.

TABLE 12

Suntan oil

| | |
|---|---|
| octyl paramethoycinnamate | 2 |
| squalane | 65 |
| N-lauroylalanine t-butyl ester | 5 |
| cetyl octanoate | 28 |
| dibutylhydroxytoluene | suitable amount |
| flavor | suitable amount |
| Total | 100(%) |

FORMULATION EXAMPLE 24

W/O Type Foundation Cream

A W/O type foundation cream having the composition shown in Table 13 below was prepared as follows. That is, the components under Component 3 were mixed, added with the components under Component 1 which had been well mixed and pulverigerd, and treated using a homomixer. The components under Component 2 were heat-dissolved and added to the mixture. The resultant mixture was treated using a homomixer, to obtain a product.

TABLE 13

W/O type foundation cream

| | |
|---|---|
| (Component 1) | |
| sericite | 5.4 |
| kaolin | 4.0 |
| titanium dioxide | 9.0 |
| red iron oxide | 0.4 |
| yellow iron oxide | 0.8 |
| black iron oxide | 0.2 |
| (Component 2) | |
| N-coconut oil fatty acid acylsarcosine isopropyl ester | 5.0 |
| decamethylcyclopentane siloxane | 12.0 |
| polyoxyethylene-modified dimethylpolysiloxane | 4.0 |
| (Component 3) | |
| antiseptic | suitable amount |
| dispersing agent | suitable amount |
| 1,3-butylene glycol | 5.0 |
| N-coconut oil fatty acid acylarginine ethyl pyrrolidone-carboxylic acid salt | 0.5 |
| purified water | balance |
| Total | 100(%) |

FORMULATION EXAMPLE 25

Powdery Foundation

A powdery foundation having the composition shown in Table 14 below was prepared as follows. That is, first, the components (pigment components) under Component 1 were mixed, and pulverized using a mill. Subsequently, the resulting product was passed to a high-speed blender. A mixture obtained by previously mixing the components under Components 2 and 3 was added to the pigment components, and these were uniformly mixed. The resulting mixture was passed through a sieve to adjust the particle size, and compression-molded to obtain a product.

TABLE 14

Powdery foundation

| | |
|---|---|
| (Component 1) | |
| talc | 20.0 |
| mica | 35.0 |
| kaolin | 5.0 |
| titanium dioxide | 9.0 |
| zinc stearate | 1.0 |
| red iron oxide | 1.0 |
| yellow iron oxide | 3.0 |
| black iron oxide | 0.2 |
| lauroyllysine | 4.0 |
| (Component 2) | |
| pyroglutamic acid glyceryl oleate | 0.5 |
| sorbitan monooleate | 2.0 |
| lanoline | 1.0 |
| N-lauroylsarcosine isopropyl ester | 6.0 |
| octyldodecyl myristate | 2.0 |
| (Component 3) | |
| antiseptic | suitable amount |
| antioxidant | suitable amount |
| flavor | suitable amount |
| Total | 100(%) |

FORMULATION EXAMPLE 26

Dual-use Foundation

A dual-use foundation having the composition shown in Table 15 below was prepared as follows. That is, the components under Component 1 were mixed, and pulverized using a mill. The mass was passed to a high-speed blender. A mixture obtained by previously mixing the components under Components 2 and 3 were added to the components in the blender, and these were uniformly mixed. The resulting mixture was passed through a sieve to adjust the particle size, and compression-molded to obtain a product.

TABLE 15

Dual-use foundation

| (Component 1) | |
|---|---|
| silicone-treated talc | 19.0 |
| silicone-treated mica | 38.0 |
| lauroyllysine | 2.0 |
| silicone-treated finely divided titanium dioxide | 20.0 |
| zinc stearate | 0.1 |
| silicone-treated red iron oxide | 1.0 |
| silicone-treated yellow iron oxide | 3.0 |
| silicone-treated black iron oxide | 0.2 |
| nylon powder | 2.0 |
| (Component 2) | |
| liquid paraffin | 3.5 |
| N-lauroylalanine ethyl ester | 0.5 |
| dimethyl polysiloxane | 4.0 |
| glycerol triisooctanoate | 5.0 |
| octyl methoxycinnamate | 1.0 |
| (Component 3) | |
| antiseptic | suitable amount |
| antioxidant | suitable amount |
| flavor | suitable amount |
| Total | 100(%) |

FORMULATION EXAMPLE 27

Rouge

A rouge having the composition shown in Table 16 below was prepared as follows. That is, titanium dioxide, kaolin, iron oxide (red), and Red No. 202 were added to a part of liquid paraffin, and dispersed therein using a roller. The other components were previously mixed, and heat-dissolved. Then, all of the components were uniformly dispersed using a homomixer. After the completion of the dispersing operation, the dispersion was cooled while being stirred to obtain a product.

TABLE 16

Rouge

| titanium dioxide | 4.2 |
|---|---|
| kaolin | 20.0 |
| lauroyllysine | 2.0 |
| iron oxide (red) | 0.3 |
| Red No. 202 | 0.5 |
| ceresine | 12.0 |
| di(cholesteryl, octyldodecyl) N-lauroylglutamate | 3.0 |
| vaseline | 20.0 |
| liquid paraffin | 25.0 |
| isopropyl myristate | 13.0 |
| N-octanoyl-β-alanine octyl ester | 2.0 |

TABLE 16-continued

Rouge

| antioxidant | suitable amount |
|---|---|
| flavor | suitable amount |
| Total | 100(%) |

FORMULATION EXAMPLE 28

Emulsified Lipstick

An emulsified lipstick having the composition shown in Table 17 below was prepared as follows. That is, the titanium dioxide, the Red No. 201 and the Red No. 202 of the components under Component 1 were added to a part of the castor oil, and dispersed therein using a roller. The Red No. 223 was dissolved into the castor oil. The other components under Component 1 were heat-dissolved, and uniformly dispersed along with the pigments and the dyes using a homomixer. The components under Component 2 were heat-dissolved, and emulsified and dispersed in the previous mixture using a homomixer. The dispersion was poured into a mold, and rapidly cooled to form a stick.

TABLE 17

Emulsified lipstick

| (Component 1) | |
|---|---|
| titanium dioxide | 3.5 |
| lauroyllysine | 1.0 |
| Red No. 201 | 0.5 |
| Red No. 202 | 2.0 |
| Red No. 203 | 0.05 |
| ceresine | 4.0 |
| candelilla wax | 8.0 |
| N-myristoyl-γ-aminobutyric acid isopropyl ester | 2.0 |
| castor oil | 30.0 |
| isostearic acid diglyceride | 39.95 |
| POE (25) POP (20) 2-tetradecyl ether | 1.0 |
| antiseptic | suitable amount |
| antioxidant | suitable amount |
| flavor | suitable amount |
| (Component 2) | |
| sodium polyaspartate solution (30%) | 1.0 |
| purified water | 4.0 |
| glycerol | 2.0 |
| propylene glycol | 1.0 |
| Total | 100(%) |

FORMULATION EXAMPLE 29

Lipstick

A lipstick having the composition shown in Table 18 below was prepared as follows. That is, the components under Component 2 were heat-dissolved. The components under Component 1 were added thereto, and kneaded and dispersed uniformly, using a roller mill, then defoamed and poured into a mold, and rapidly cooled to form a lipstick.

TABLE 18

Lipstick

| (Component 1) | |
|---|---|
| titanium dioxide | 5.0 |
| Red No. 201 | 0.6 |
| Red No. 202 | 1.0 |
| Red No. 223 | 0.2 |
| (Component 2) | |
| solid paraffin | 8.0 |
| candelilla wax | 9.0 |
| bees wax | 5.0 |
| carnauba wax | 5.0 |
| castor oil | 25.0 |
| N-octanoyl-β-methyl-β-alanine isopropyl ester | 20.0 |
| Isopropyl myristate | 10.0 |
| liquid lanoline | 11.0 |
| antiseptic | suitable amount |
| antioxidant | suitable amount |
| flavor | suitable amount |
| Total | 100(%) |

FORMULATION EXAMPLE 30

Eyebrow Pencil

An eybrow pencil having the composition shown in Table 19 below was prepared as follows. That is, the powdery components under Component 1 were mixed well using a blender. The mixture was subjected to dispersing operation together with the other components which had been heat-dissolved, using a mill. The mass was compression-molded to obtain a product.

TABLE 19

Eyebrow pencil

| titanium dioxide | 20.0 |
|---|---|
| iron oxide (red) | 20.0 |
| iron oxide (yellow) | 20.0 |
| iron oxide (black) | 15.0 |
| talc | 10.0 |
| lanoline wax | 10.0 |
| N-coconut oil fatty acid acylalanine isopropyl ester | 4.0 |
| glycerol monostearate | 1.0 |
| antiseptic | suitable amount |
| antioxidant | suitable amount |
| flavor | suitable amount |
| Total | 100(%) |

FORMULATION EXAMPLE 31

O/W Type Foundation Cream

An O/W type foundation cream having the composition shown in Table 20 below was prepared as follows. That is, the propylene glycol having the bentonite dispersed therein among the components under Component 2 was added to the purified water, and treated at 70° C. using a homomixer. Then, the other components under Component 2 were added thereto, and fully stirred. To this were added the components under Component 1 which had been mixed and pulverized while being stirred, and the mixture was treated at 70° C. using a homomixer. Subsequently, the components under Component 3 which had been heated to from 70 to 80° C. were gradually added thereto, treated at 70° C. using a homomixer, and cooled to room temperature to obtain a product.

TABLE 20

O/W type foundation

| (Component 1) | |
|---|---|
| talc | 3.0 |
| titanium dioxide | 5.0 |
| red iron oxide | 0.5 |
| yellow iron oxide | 1.4 |
| black iron oxide | 0.1 |
| (Component 2) | |
| bentonite | 0.5 |
| polyoxyethylenesorbitan monostearate | 0.9 |
| triethanolamine | 1.0 |
| propylene glycol | 10.0 |
| purified water | 54.4 |
| (Component 3) | |
| stearic acid | 2.2 |
| isohexadecyl alcohol | 7.0 |
| glycerol monostearate | 2.0 |
| liquid lanoline | 2.0 |
| liquid paraffin | 6.0 |
| N-lauroylalanine propyl ester | 2.0 |
| antiseptic | suitable amount |
| Total | 100(%) |

FORMULATION EXAMPLE 32

Conditioning Shampoo

A conditioning shampoo having the composition shown in Table 21 below was prepared as follows. That is, the purified water was added with the cationized cellulose and heated with stirring, to 70° C. To this was added the other components and dissolved by stirring. The mass was cooled to obtain a product.

TABLE 21

Conditioning shampoo

| lauryl POE(3) sulfuric acid ester triethanolamine salt (aqueous 30% solution) | 10.0 |
|---|---|
| lauryl POE(3) sulfuric acid ester sodium salt (aqueous 30% solution) | 10.0 |
| coconut oil fatty acid acylalanine triethanolamine salt (aqueous 30% solution) | 10.0 |
| lauryl sulfuric acid ester sodium salt (aqueous 30% solution) | 5.0 |
| lauryl diethanol amide | 3.0 |
| lauryl dimethyl aminoacetic acid betaine | 7.0 |
| cationized cellulose | 0.2 |
| ethylene glycol distearic acid ester | 2.0 |
| N-lauroyl-N-methyl-β-alanine isopropyl ester | 2.0 |
| flavor | suitable amount |
| antiseptic | suitable amount |
| pH modifier | suitable amount |
| purified water | balance |
| Total | 100(%) |

FORMULATION EXAMPLE 33

Rinse in Shampoo

A rinse in shampoo having the composition shown in Table 22 below was prepared as follows. That is, the stearyltrimethylammonium chloride and the amphoteric surfactant were added to the purified water, heat-dissolved, and maintained at 70° C. The other components were added thereto, dissolved, and then cooled to obtain a product.

TABLE 22

Rinse in shampoo

| | |
|---|---|
| 2-alkyl-N-carboxymethyl-N-hydroxyethylimidazolinium betaine | 16.0 |
| coconut oil fatty acid diethanolamide | 4.0 |
| N-coconut oil fatty acid acylarginine ethylpyrrolidonecarboxylic acid salt | 1.0 |
| stearyltrimethylammonium chloride | 2.0 |
| N-lauroyl-N-methyl-β-alanine sodium salt | 1.0 |
| N-lauroylsarcosine isopropyl ester | 1.0 |
| POE alkylpolyamine | 1.0 |
| flavor | suitable amount |
| pigment | suitable amount |
| pH modifier | suitable amount |
| purified water | balance |
| Total | 100(%) |

FORMULATION EXAMPLE 34

Hair Treatment Cream

A hair treatment cream having the composition shown in Table 23 below was prepared as follows. That is, the components under Component 1 and those under Component 2 were heated to 80° C., respectively. The components under Component 2 was with stirring, added gradually with the components under Component 1, and the mixture was cooled to obtain a product.

TABLE 23

Hair treatment cream

| | |
|---|---|
| (Component 1) | |
| N-coconut oil fatty acid acylalanine isopropyl ester | 9.0 |
| cetyl octanoate | 4.0 |
| POE(5) oleic acid ester | 4.0 |
| cetostrearyl alcohol | 3.0 |
| cetanol | 2.0 |
| stearic acid propylene glycol | 2.0 |
| glycerol stearate | 1.0 |
| stearic acid polyethylene glycol | 1.0 |
| distearyl dimethyl ammonium chloride | 2.0 |
| (Component 2) | |
| N-coconut oil fatty acid acylarginine ethyl pyrrolidone carboxylic acid salt | 0.5 |
| 1,3-butylene glycol | 5.0 |
| chitin (aqueous 1% solution) | 10.0 |
| flavor | suitable amount |
| antiseptic | suitable amount |
| purified water | balance |
| Total | 100(%) |

FORMULATION EXAMPLE 35

Hair Lotion

A hair lotion having the composition shown in Table 24 below was prepared as follows. That is, the components under Component 1 and those under Component 2 were heated to 80° C., respectively. The components under Component 2 was with stirring, added gradually with the components under Component 1, and the mixture was cooled to obtain a product.

TABLE 24

Hair lotion

| | |
|---|---|
| (Component 1) | |
| N-lauroylsarcosine isopropyl ester | 15.0 |
| Vaseline | 5.0 |
| POE(20) sorbitan monolauric acid ester | 10.0 |
| isopropyl myristate | 10.0 |
| bees wax | 1.0 |
| stearic acid | 1.0 |
| stearic acid propylene glycol | 1.0 |
| stearic acid polyethylene glycol | 1.0 |
| diglycerol oleate | 4.0 |
| hydrogenated soybean lecithin | 1.0 |
| (Component 2) | |
| N-stearoylglutamic acid sodium salt | 0.4 |
| xanthane gum (aqueous 1% solution) | 5.0 |
| carboxyvinyl polymer (aqueous 1% solution) | 5.0 |
| sodium polyaspartate solution (1%) | 1.0 |
| 1,3-butylene glycol | 5.0 |
| flavor | suitable amount |
| antiseptic | suitable amount |
| purified water | balance |
| Total | 100(%) |

FORMULATION EXAMPLE 36

Cleansing Foam

A cleansing foam having the composition shown in Table 25 below was prepared as follows. That is, the components under Component 1 and those under Component 2 were heated to 80° C., respectively. The components under Component 2 was with stirring, added gradually with the components under Component 1, and the mixture was cooled to obtain a product.

TABLE 25

Cleansing foam

| | |
|---|---|
| (Component 1) | |
| stearic acid | 12.0 |
| lauric acid | 3.0 |
| myristic acid | 14.0 |
| N-myristoylglycine octyl ester | 2.0 |
| POP(20) glycerol monostearate | 2.0 |
| N-lauroyl-N-methyltaurine sodium salt (aqueous 30% solution) | 4.0 |
| (Component 2) | |
| sodium hydroxide | 5.0 |
| 1,3-butylene glycol | 10.0 |
| sorbitol (aqueous 70% solution) | 15.0 |
| glycerol | 10.0 |
| flavor | suitable amount |
| antiseptic | suitable amount |
| purified water | balance |
| Total | 100(%) |

FORMULATION EXAMPLE 37

Cleansing Oil

A cleansing oil having the composition shown in Table 26 below was prepared in an ordinary manner.

TABLE 26

| Cleansing oil | |
| --- | --- |
| N-coconut oil fatty acid acyl-N-methyl-β-alanine isopropyl ester | 50.0 |
| 2-ethylhexyl stearate | 20.0 |
| dimethylpolysiloxane | 20.0 |
| POE oleyl alcohol ether | 10.0 |
| flavor | suitable amount |
| antiseptic | suitable amount |
| Total | 100(%) |

FORMULATION EXAMPLE 38

Makeup Cleansing Product

A makeup cleansing product having the composition shown in Table 27 below was prepared as follows. That is, the components under Component 1 and those under Component 2 were heated to 80° C., respectively. While the components under Component 2 were stirred, the components under Component 1 were gradually added thereto, and the mixture was cooled to obtain a product.

TABLE 27

| Makeup cleansing product | |
| --- | --- |
| (Component 1) | |
| POE cetyl alcohol ether | 4.0 |
| sodium N-stearoylglutamate | 1.5 |
| N-coconut oil fatty acid acylglutamic acid triethanolamine (aqueous 30% solution) | 20.0 |
| myristic acid | 2.0 |
| arginine | 0.5 |
| lysine | 0.5 |
| purified water | balance |
| antiseptic | suitable amount |
| (Component 2) | |
| N-lauroylsarcosine isopropyl ester | 5.0 |
| isostearic acid | 8.5 |
| liquid paraffin | 50.0 |
| Total | 100(%) |

FORMULATION EXAMPLE 39

Shaving Foam

A shaving foam having the composition shown in Table 28 below was prepared as follows. That is, the glycerol, the triethanolamine and the compound of Synthesis Example 8 were added to the purified water, and the solution was heated to 70° C. This solution was used as the aqueous phase portion. The other components were heat-dissolved, and the mixture was used as the oily phase portion. The oily phase portion was added to the aqueous phase portion, and a neutralization reaction was conducted. The filling operation was conducted in such way that the stock solution was charged into a can, a valve was fitted thereto, and the gas was then filled therein.

TABLE 28

| Shaving foam | |
| --- | --- |
| (Stock solution) | |
| stearic acid | 4.5 |
| coconut oil fatty acid | 1.5 |
| glycerol monostearate | 5.0 |
| glycerol | 10.0 |
| N-stearoylalanine octyl ester | 0.5 |
| triethanolamine | 4.0 |
| flavor | suitable amount |
| purified water | balance |
| Total | 100(%) |
| (Filling) | |
| stock solution | 96.0 |
| liquefied petroleum gas | 4.0 |
| Total | 100(%) |

FORMULATION EXAMPLE 40

Liquid Detergent

A liquid detergent having the composition shown in Table 29 below was prepared in a usual manner.

TABLE 29

| Liquid detergent | |
| --- | --- |
| N-lauroylglutamic acid triethanolamine (aqueous 30% solution) | 20.0 |
| N-lauroylmethyltaurine sodium salt (aqueous 30% solution) | 5.0 |
| N-coconut oil fatty acid acylglycine potassium salt (aqueous 30% solution) | 5.0 |
| lauric acid triethanolamine | 10.0 |
| myristic acid triethanolamine | 10.0 |
| lauroylimidazolinium betaine | 5.0 |
| lauroyldiethanolamide | 5.0 |
| propylene glycol | 5.0 |
| N-coconut oil fatty acid acyl-N-methyl-β-alanine isopropyl ester | 1.0 |
| flavor | suitable amount |
| dye | suitable amount |
| antiseptic | suitable amount |
| metallic ion blocking agent | suitable amount |
| purified water | balance |
| Total | 100(%) |

FORMULATION EXAMPLE 41

Bath Oil

A bath oil having the composition shown in Table 30 below was prepared in an ordinary manner.

TABLE 30

| Bath oil | |
| --- | --- |
| liquid paraffin | 50.0 |
| N-coconut oil fatty acid acylalanine isopropyl ester | 10.0 |
| squalane | 10.0 |
| macadamia nut oil | 10.0 |
| sorbitan oleate | 5.0 |
| POE oleyl ether | 10.0 |
| flavor | 4.0 |
| purified water | 1.0 |
| Total | 100(%) |

FORMULATION EXAMPLE 42

Soap

A soap having the composition shown in Table 31 below was prepared in an ordinary manner.

TABLE 31

Soap

| | |
|---|---|
| beef tallow | 22.0 |
| N-lauroylsarcosine isopropyl ester | 6.0 |
| coconut oil | 4.0 |
| castor oil | 4.0 |
| olive oil | 4.0 |
| sodium hydroxide | 6.0 |
| ethyl alcohol | 20.0 |
| purified water | 20.0 |
| sugar | 9.0 |
| glycerol | 4.0 |
| flavor | 1.0 |
| dyestuff | suitable amount |
| metallic ion blocking agent | suitable amount |
| Total | 100(%) |

FORMULATION EXAMPLE 43

Setting Agent

A setting agent having the composition shown in Table 32 below was prepared. That is, into the ethyl alcohol were dissolved the other components, and the solution was filtered. After the filtration, the stock solution was filled in a can, a valve was fitted thereto, and the gas was then filled therein.

TABLE 32

Setting agent

| | |
|---|---|
| (Stock solution) | |
| acrylic resin alkanolamine solution (50%) | 8.0 |
| polyoxyethylene hardened castor oil | suitable amount |
| liquid paraffin | 4.0 |
| N-lauroylalanine ethyl ester | 1.0 |
| glycerol | 3.0 |
| flavor | suitable amount |
| antiseptic | suitable amount |
| ethyl alcohol | 15.0 |
| purified water | 69.0 |
| Total | 100(%) |
| (Filling) | |
| stock solution | 90.0 |
| liquefied petroleum gas | 10.0 |
| Total | 100(%) |

FORMULATION EXAMPLE 44

Permanent Liquid

A permanent liquid having the composition shown in Table 33 below was prepared in a usual manner.

TABLE 33

Permanent liquid

| | |
|---|---|
| (First agent) | |
| sodium thioglycolate | 7.0 |
| aqueous ammonia (25%) | 2.0 |
| N-2-ethylhexanoylsarcosine isopropyl ester | 1.0 |
| oleyl alcohol | 0.5 |
| polyoxyethylene (20) lauryl ether | 0.5 |
| disodium edetate | 0.1 |
| propylene glycol | 3.0 |
| coloring matter | suitable amount |
| flavor | suitable amount |
| purified water | balance |
| (Second agent) | |
| sodium bromate | 6.0 |
| coloring matter | suitable amount |
| flavor | suitable amount |
| purified water | balance |
| Total | 100(%) |

FORMULATION EXAMPLE 45

Face Washing Agent

A face washing agent having the composition shown in Table 34 below was prepared in a usual manner. That is, the components under Component 1 and those under Component 2 were heated to 80° C., respectively. While the components under Component 2 were stirred, the components under Component 1 were gradually added thereto, and cooled to obtain a product.

TABLE 34

Face washing agent

| | |
|---|---|
| (Component 1) | |
| sodium N-lauroylglutamate | 20.0 |
| N-lauroyl-N-methyltaurine sodium salt (aqueous 30% solution) | 5.0 |
| POE · POP block polymer | 5.0 |
| POE (15) oleyl alcohol ether | 3.0 |
| N-lauroylsarcosine isopropyl ester | 1.0 |
| (Component 2) | |
| glycerol | 10.0 |
| polyethylene glycol 400 | 15.0 |
| antiseptic | suitable amount |
| chelating agent | suitable amount |
| flavor | suitable amount |
| coloring matter | suitable amount |
| purified water | balance |
| Total | 100(%) |

FORMULATION EXAMPLE 46

Hair Dye

A hair dye having the composition shown in Table 35 below was prepared in a usual manner.

TABLE 35

Hair dye

| | |
|---|---|
| para-phenylenediamine | 3.0 |
| resorcin | 0.2 |
| oleic acid | 20.0 |
| POE (10) oleyl alcohol ether | 13.0 |

TABLE 35-continued

| Hair dye | |
|---|---|
| N-coconut oil fatty acid-N-methyl-β-alanine isopropyl ester | 1.0 |
| glycine betaine | 1.0 |
| isopropyl alcohol | 10.0 |
| aqueous ammonia (28%) | 10.0 |
| purified water | 41.5 |
| antioxidant | suitable amount |
| chelating agent | suitable amount |
| Total | 100(%) |

The cosmetic compositions of Formulation Examples 16 to 46 were excellent in the hair conditioning effect or the skin feeling upon use.

SYNTHESIS EXAMPLE 23

Synthesis of N-stearoylalanine methyl ester

Sixty(60) grams of N-stearoylalanine and 750 ml of methanol were charged into a 1,000-milliliter flask. Further, 2 ml of conc. sulfuric acid were added as the catalyst. The mixture was heated under reflux for reaction for 8 hours.

After the completion of the reaction, the reaction mixture was allowed to stand to room temperature. The excess methanol was distilled off under reduced pressure. The residue was dissolved in 500 ml diethyl ether and neutralized with approximately 500 ml of an aqueous saturated solution of sodium hydrogencarbonate. The resulting organic phase was washed with water, and dried over approximately 30 g of anhydrous magnesium sulfate. The anhydrous magnesium sulfate was then filtered off. The ether was distilled away from the mother liquor. The residue was recrystallized from ethanol and dried under reduced pressure to obtain 50 g (80% yield) of the captioned compound as a solid.

IR (KBr): 2940 cm$^{-1}$ (C—H), 1730 cm$^{-1}$ (ester), 1620 cm$^{-1}$ (amide).

SYNTHESIS EXAMPLE 24

Synthesis of N-coconut oil fatty acid acylglutamic acid isopropyl diester

Fifty(50) grams of N-coconut oil fatty acid acylglutamic acid and 400 ml of isopropanol were charged into a 500-milliliter flask. Further, 2 ml of conc. sulfuric acid were added as the catalyst. The mixture was heated under reflux for reaction for 8 hours.

After the completion of the reaction, the reaction mixture was allowed to stand to room temperature. After the reaction mixture had got cool, the insoluble impurities were filtered off and the excess isopropanol was distilled off under reduced pressure. The concentrate was neutralized with approximately 200 ml of an aqueous saturated solution of sodium hydrogencarbonate. The resulting oil phase was separated, washed with water, and dried under reduced pressure to obtain 35 g of the captioned compound as a transparent liquid or paste.

ESI-MS: 358, 386, 414, 442, 470 (M+H)+.

IR (neat): 2910 cm$^{-1}$ (C—H), 1730 cm$^{-1}$ (ester), 1630 cm$^{-1}$ (amide).

EXAMINATION EXAMPLE 4

Examination of Solubility

The solubility of a UV-A absorbent 2-ethylhexyl dimethoxybenzylidenedioxoimidazolidinepropionate "Soft Shade DH" (ex Ajinomoto Co., Inc.) in various oily materials was examined. The results are shown in Table 36 below.

TABLE 36

| Solubility in various oily materials | |
|---|---|
| Oily materials | Solubility |
| cocoylalanine isopropyl ester | ○ |
| lauroylsarcosine isopropyl ester | ○ |
| N-lauroyl-N-methyl-β-alanine isopropyl | ○ |
| cocoylglutamic acid diisopropyl ester | Δ |
| lauroylsarcosine isostearyl ester | X |
| lauroylsarcosine octyldodecyl ester | X |
| dihexyldecyl lauroylglutamate | X |
| isopropyl myristate | X |
| glycerol stearate | X |
| liquid paraffin | X |

Evaluation standard of solubility:
X The amount of the compound dissolved in 100 g of the oily material is less than 5 g.
Δ It is at least 5 g and less than 10 g.
○ It is at least 10 g.

EXAMINATION EXAMPLES 5 to 8

Examination of Stickiness

Ultraviolet ray-absorbing products (4 inventive products) each having a composition shown in Table 37 below were prepared. Five panelists coated a suitable amount of each of these products on the back of their hand to examine the lack of stickiness.

That is, an average value in the evaluation of each panelist according to the following evaluation standard (footnote to Table 37 below) was calculated. When the average value was between 1.0 and 2.0, it was rated as ○; when the average value was at least 0.5 and less than 1.0, it was rated as Δ; and when the average value was at least –0.5 and less than 0.5, it was rated as x. The results are also shown in Table 37. In this table, the unit of the amount of the components is weight % (this also applies to Tables 38 to 40).

TABLE 37

| | Stickiness | | | |
|---|---|---|---|---|
| | Examination Example | | | |
| Component | 5 | 6 | 7 | 8 |
| 4-t-butyl-4'-methoxydibenzoylmethane (*) | 10 | 10 | 10 | 10 |
| cocoylalanine isopropyl ester | 90 | | | |
| lauroylsarcosine isopropyl ester | | 90 | | |
| N-lauroyl-N-methyl-β-alanine isopropyl | | | 90 | |
| cocoylglutamic acid diisopropyl ester | | | | 90 |
| lauroylsarcosine isostearyl ester | | | | |
| lauroylsarcosine octyldodecyl ester | | | | |
| dihexyldecyl lauroylglutamate | | | | |
| isopropyl myristate | | | | |
| glycerol stearate | | | | |
| liquid paraffin | | | | |
| Lack of stickiness | ○ | ○ | ○ | ○ |

(*) UV-A absorbent "Parsol 1789" (solid), made by Givaudan Evaluation standard of stickiness:
2: No stickiness is provided.
1: Stickiness is not provided so much.
0: Stickiness is slightly provided.
–1: Stickiness is provided.
–: completely undissolved.

COMPARATIVE EXAMPLES 1 to 9

Examination of Stickiness

UV absorbing compositons (9 comparative items) each having one of the compositions shown in Table 38 below were prepared and examined with respect to their lack of stickiness. The results are also shown in the same table.

TABLE 38

Stickiness

| Component | Comparative Example | | | | | | | | |
|---|---|---|---|---|---|---|---|---|---|
| | 1 | 2 | 3 | 4 | 5 | 6 | 7 | 8 | 9 |
| 4-t-butyl-4'-methoxydibenzoylmethane (*) | 10 | 10 | 10 | 10 | 10 | 10 | 1 | 1 | 1 |
| cocoylalanine isopropyl ester | | | | | | | | | |
| lauroylsarcosine isopropyl ester | | | | | | | | | |
| N-lauroyl-N-methyl-β-alanine Isopropyl | | | | | | | | | |
| cocoylglutamic acid diisopropyl ester | | | | | | | | | |
| lauroylsarcosine isostearyl ester | 90 | | | | | | | | |
| lauroylsarcosine octyldodecyl ester | | 90 | | | | | | | |
| dihexyldecyl lauroylglutamate | | | 90 | | | | | | |
| isopropyl myristate | | | | 90 | | | 99 | | |
| glycerol stearate | | | | | 90 | | | 99 | |
| liquid paraffin | | | | | | 90 | | | 99 |
| Lack of stickiness | Δ | Δ | Δ | — | — | — | X | X | X |

The footnote to this table is the same as that to Table 37.

EXAMINATION EXAMPLES 9 to 12

Examination of Stickiness

Ultraviolet-absorbing compositions (4 inventive items) each having one of the a compositions shown in Table 39 below were prepared, and the lack of stickiness thereof was examined. The results are also shown in the same table.

TABLE 39

Stickiness

| Component | Examination Example | | | |
|---|---|---|---|---|
| | 9 | 10 | 11 | 12 |
| octyl methoxycinnamate (*) | 10 | 10 | 10 | 10 |
| cocoylalanine isopropyl ester | 90 | | | |
| lauroylsarcosine isopropyl ester | | 90 | | |
| N-lauroyl-N-methyl-β-alanine isopropyl | | | 90 | |
| cocoylglutamic acid diisopropyl ester | | | | 90 |
| lauroylsarcosine isostearyl ester | | | | |
| lauroylsarcosine octyldodecyl ester | | | | |
| dihexyldecyl lauroylglutamate | | | | |
| isopropyl myristate | | | | |
| glycerol stearate | | | | |
| liquid paraffin | | | | |
| Lack of stickiness | ○ | ○ | ○ | ○ |

(*) UV-A absorbent "Parsol MCX" (liquid), made by Givaudan Evaluation standard of stickiness is the same as that in the footnote to Tabal 37.

COMPARATIVE EXAMPLES 10 to 15

Examination of Stickiness

Ultraviolet-absorbing products (6 comparative products) each having a composition shown in Table 40 below were prepared, and the lack of stickiness thereof was examined. The results are also shown in the same table.

TABLE 40

Stickiness

| Component | Comparative Example | | | | | |
|---|---|---|---|---|---|---|
| | 10 | 11 | 12 | 13 | 14 | 15 |
| octyl methoxycinnamate | 10 | 10 | 10 | 10 | 10 | 10 |
| cocoylalanine isopropyl ester | | | | | | |
| lauroylsarcosine isopropyl ester | | | | | | |
| N-lauroyl-N-methyl-β-alanine isopropyl | | | | | | |
| cocoylglutamic acid diisopropyl ester | | | | | | |
| lauroylsarcosine isostearyl ester | 90 | | | | | |
| lauroylsarcosine octyldodecyl ester | | 90 | | | | |
| dihexyldecyl lauroylglutamate | | | 90 | | | |
| isopropyl myristate | | | | 90 | | |
| glycerol stearate | | | | | 90 | |
| liquid paraffin | | | | | | 90 |
| Lack of stickiness | Δ | Δ | Δ | X | X | X |

The footnote to this table is the same as that to Table 39.

Formulation Examples of various cosmetic compositions will be described below. In the composition of the components, % means % by weight (totaling 100%).

FORMULATION EXAMPLE 47

Cream

A cream was prepared in a usual manner according to the composition shown in Table 41 below. That is, the components under Component 1 and those under Component 2 were heated to 70° C., respectively. While the components under Component 1 were stirred, the components under Component 2 were gradually added thereto for emulsification. This cream showed an excellent organoleptic property without stickiness.

TABLE 41

Cream

| (Component 1) | |
|---|---|
| cetanol | 0.5% |
| vaseline | 2 |
| N-lauroylsarcosine isopropyl ester | 4 |
| 2-ethylhexyl dimethoxybenzylidenedioxoimidazolidine propionate (*) | 4 |
| glycerol monostearate | 2.5 |
| POE (20) sorbitan monostearic acid ester | 1.5 |
| aloe extract | 0.2 |
| (Component 2) | |
| glycerol | 10 |
| carboxyvinyl polymer (aqueous 1% solution) | 30 |
| aqueous 10% sodium hydroxide solution | suitable amount |
| antiseptic | suitable amount |
| purified water | balance |

(*) UV absorbent "Soft Shade DH", made by Ajinomoto Co., Inc.

FORMULATION EXAMPLE 48

W/O Type Cream

A W/O type cream having the composition shown in Table 42 below was prepared in an ordinary manner. That is, the components under Component 1 and those under Component 2 were heated to 70° C., respectively. The components under Component 1 were, with stirring, gradually with the components under 2 to emulsify. This W/O type cream was organoleptically excellent without stickiness.

TABLE 42

W/O type cream (Component 1)

| | |
|---|---|
| lanoline alcohol | 5% |
| liquid paraffin | 15 |
| bees wax | 8 |
| N-cocoylalanine isopropyl ester | 20 |
| sorbitan sesquioleate | 2 |
| octyl paramethoxycynnamate | 6 |
| oxybenzone | 3 |

(Component 2)

| | |
|---|---|
| borax | 0.4 |
| propylene glycol | 5 |
| antiseptic | suitable amount |
| flavor | suitable amount |
| purified water | balance |

FORMULATION EXAMPLE 49

Lotion

A lotion having the composition shown in Table 43 below was prepared in an ordinary manner. That is, the components under Component 1 and those under Component 2 were heated to 70° C., respectively. The components under Component 1 was, with stirring, added gradually with the components under Component 2. The mixture was, with stirring, cooled to 50° C. at which the components under Component 3 was added to obtain a lotion. This lotion was organoleptically excellent without stickiness.

TABLE 43

Lotion (Component 1)

| | |
|---|---|
| glycerol dilaurate | 2% |
| paradimethylamino acid benzoic acid octyl | 5 |
| cetanol | 0.5 |
| N-cocoylalanine isopropyl ester | 5 |
| N-lauroyl-L-glutamic acid di(phytosteryl, octyldodecyl) | 1.5 |
| tocopheryl acetate | 0.1 |
| POE(23)lauryl ether | 2 |
| stearic acid | 3 |

(Component 2)

| | |
|---|---|
| purified water | balance |
| antiseptic | 0.2 |
| sorbitol(70%) | 4 |
| xanthan gum | 0.3 |
| triethanolamine | 0.6 |

(Component 3)

| | |
|---|---|
| flavor | 0.3 |

FORMULATION EXAMPLE 50

Sun Oil

A sun oil having the composition shown in Table 44 below was prepared in an ordinary manner. That is, the components shown in the table were dissolved uniformly by heating to 60° C. Thus sun oil was organoleptically excellent without stickiness.

TABLE 44

Sun oil

| | |
|---|---|
| 2-ethylhexyl dimethoxybenzylidenedioxoimidazolinepropionate(*) | 4% |
| cacao butter | 3 |
| flavor | 0.5 |
| N-lauroylsarcosine isopropyl ester | 40 |
| fatty acid(c8~12) triglyceride | 52.5 |

(*)"Soft Shade DH", a UV absorbent ex Ajinomoto Co., Ltd.

FORMULATION EXAMPLE 51

Creamy Foundation

A creamy foundation having the composition shown in Table 45 below was prepared in an ordinary manner. That is, the components under Component 1 and those under Component 2 were dissolved by heating to 70° C., respectively. The components under Component 2 were, with stirring, added gradually with the components under component 1 to emolsify. The mixed powder under Component 3 was dispersed therein and cooled to obtain a creamy foundation. This creamy foundation was organoleptically excellent without stickiness.

TABLE 45

Creamy foundation (Component 1)

| | |
|---|---|
| stearyl alcohol | 2% |
| glycerol monostearate | 2 |
| stearic acid | 2 |
| N-lauuroyl-N-methyl-β-alanine isopropyl ester | 5 |
| safflower oil | 4 |
| 4-t-butyl-4'-methoxydibenzoylmethane(*) | 2 |
| antiseptic | suitable amount |
| flavor | suitable amount |

(Component 2)

| | |
|---|---|
| glycerol | 5 |
| potassium hydroxide | 0.2 |
| purified water | balance |

(Component 3)

| | |
|---|---|
| mixed powder | 10 |

(*)"Parsol 1789" (solid, a UV absorbent ex Givaudan.

FORMULATION EXAMPLE 52

Lipstick

A lipstick was prepared in a usual manner according to the composition shown in Table 46 below. That is, the components other than the mixed powder shown in this table were heat-dissolved, and uniformly mixed. To this was added the mixed powder, and they were kneaded and uniformly dispersed using a roll mill. Then, the mixture was poured into a mold, and rapidly cooled to obtain a lipstick. This lipstick showed an excellent organoleptic property without stickiness.

TABLE 46

Lipstick

| | |
|---|---|
| solid paraffin | 20% |
| vaseline | 20 |
| castor oil | 23 |

TABLE 46-continued

| Lipstick | |
|---|---|
| N-cocoylsarcosine isopropyl ester | 20 |
| glycerol triisostearate | 5 |
| 2-ethylhexyl dimethoxybenzylidenedioxoimidazolidine-propionate (*) | 5 |
| flavor | suitable amount |
| mixed powder | 7 |

(*) UV absorbent "Soft Shade DH", made by Ajinomoto Co., Inc.

EXAMINATION EXAMPLE 13

Evaluation of Properties of Various Oily Materials

With respect to various oily materials including some N-acylamino acid esters of the present invention, powdery compositions formed by blending each oily material with a powder pigment of titanium dioxide ($TiO_2$) were evaluated or examined from various aspects. This will be described in detail below.

(a) Evaluation of Pigment Dispersibility

Liquid paraffin "SILKOOL P55" (made by Matsumura Yushi Kenkyusho) was added to 10 g of $TiO_2$ "TTO-55N" (made by Ishihara Sangyo Kaisha Ltd.) containing 10% by weight of one of the oily materials (as the oily phase component) shown in Table 47. The minimum value in terms of parts by weight in which the powder was put together was defined as wetting point. The wetting point was indicated in terms of the numeral of parts by weight of liquid paraffin added to 100 parts by weight of the initial powder containing 10% by weight of an oily material. Liquid paraffin was further added thereto from the wetting point, and the minimum numeral of parts by weight of the liquid paraffin in which the mixture came to show a fluidity was defined as flowing point. It was indicated in terms of the accumulative numeral value of parts by weight of the liquid paraffin added to 100 parts by weight of the initial powder containing 10% by weight of an oily material.

The smaller the difference between the wetting point and the flowing point, the better the dispersibility ("Science of Fragrance", published by Fragrance Journal in 1990, p. 390). Accordingly, the index of pigment dispersibility was evaluated in terms of the difference between the wetting point and the flowing point. That is, in Table 47, when the difference between the wetting point and the flowing point was up to 35, it was rated as ⊙⊙; when the difference was between 36 and 45, it was rated as ⊙; and when the difference was between 46 and 55, it was rated as Δ; and when the difference was 56 or more, it was rated as ×.

TABLE 47

| | Oily material | Pigment dispersibility |
|---|---|---|
| Inventive product 1 | cocoylalanine isopropyl ester | ⊙⊙ |
| Inventive product 2 | lauroylsarcosine isopropyl ester | ⊙⊙ |
| Inventive product 3 | lauroyl-N-methyl-β-alanine isopropyl ester | ⊙⊙ |
| Inventive product 4 | cocoylglutamic acid isopropyl diester | ⊙⊙ |
| Comparative product 1 | lauroylsarcosine isostearyl ester | Δ |
| Comparative product 2 | lauroylglutamic acid octyldodecyl diester | Δ |
| Comparative product 3 | myristic acid isopropyl ester | Δ |
| Comparative product 4 | castor oil | × |
| Comparative product 5 | academian nut oil | ⊙ |
| Comparative product 6 | purified lanoline | × |
| Comparative product 7 | liquid paraffin | × |

(b) Examination of Clean Feeling and the Like

Each oily material (25% by weight), 25% by weight of $TiO_2$ and 50% by weight of liquid paraffin were mixed in such way that $TiO_2$ became uniform to prepare an inorganic pigment composition. Five panelists coated an appropriate amount of each of these compositions on the back of their hand, and clean feeling, stickiness, smoothness, extensibility and adaptability thereof were examined.

That is, <evaluation standard of stickiness> was; 2: no stickiness is provided, 1: stickiness is not provided so much, 0: stickiness is slightly provided, and −1: stickiness is provided. An average value according to this evaluation standard in the evaluation of each panelist was calculated. When the average value was between 1.5 and 2.0, it was rated as ⊙⊙; when the average value was at least 1.0 and less than 1.5, it was rated as ⊙; when the average value was at least 0.5 and less than 1.0, it was rated as Δ; and when the average value was at least −1 and less than 0.5, it was rated as ×. The results are shown in Table 48.

Further, <evaluation standard of clean feeling>, <evaluation standard of smoothness>, <evaluation standard of extensibility> and <evaluation standard of adaptability> were the same; and 2: very good, 1: good, 0: common, and −1: bad. An average value in the evaluation of each panelist according to this evaluation standard was calculated. When the average value was between 1.5 and 2.0, it was rated as ⊙⊙; when the average value was at least 1.0 and less than 1.5, it was rated as ⊙; when the average value was at least 0.5 and less than 1.0, it was rated as Δ; and when the average value was at least −1.0 and less than 0.5, it was rated as ×. The results are shown in Table 48.

TABLE 48

| | Oily component | Clean feeling | Stickiness | Smoothness | Extensibility | adaptability |
|---|---|---|---|---|---|---|
| Inventive Product 1 | Cocoylalanine isopropyl ester | ⊙⊙ | ⊙⊙ | ⊙ | ⊙⊙ | ⊙⊙ |
| Inventive product 2 | Lauroylsarcosine isopropyl ester | ⊙⊙ | ⊙⊙ | ⊙⊙ | ⊙⊙ | ⊙⊙ |
| Inventive product 3 | Lauroyl-N-methyl-β-alanine isopropyl ester | ⊙⊙ | ⊙⊙ | ⊙⊙ | ⊙⊙ | ⊙⊙ |
| Inventive product 4 | Cocoylglutamic acid isopropyl diester | ⊙ | ⊙ | ⊙⊙ | ⊙⊙ | ⊙⊙ |

TABLE 48-continued

| | Oily component | Clean feeling | Stickiness | Smoothness | Extensibility | adaptability |
|---|---|---|---|---|---|---|
| Comparative product 1 | lauroylsarcosine isostearyl ester | Δ | Δ | Δ | Δ | Δ |
| Comparative product 2 | lauroylglutamic acid octyldodecyl diester | Δ | Δ | Δ | ○ | ○ |
| Comparative product 3 | myristic acid isopropyl ester | ○ | ○ | Δ | Δ | ○ |
| Comparative product 4 | castor oil | X | X | Δ | Δ | Δ |
| Comparative product 5 | academian nut oil | Δ | X | X | X | X |
| Comparative product 6 | purified lanoline | X | X | X | Δ | Δ |
| Comparative product 7 | liquid paraffin | X | X | X | X | X |

Formulation Examples of various cosmetic compositions will be shown below. In the composition of the components, % means % by weight (totaling 100%).

FORMULATION EXAMPLE 53

Foundation

A foundation was prepared in a usual manner according to the composition shown in Table 49 below. That is, the components under Component A were mixed using a blender, and the components under Component B were added thereto to adjust the color. These were uniformly mixed. The mixture was pulverized using a mill, and compression-molded in an inside dish. This foundation had a good pigment dispersion state without color unevenness, and was also excellent in feeling upon use.

TABLE 49

| Foundation | |
|---|---|
| (Component A) | |
| talc | 36.9% |
| sericite | 30 |
| mica | 10 |
| magnesium stearate | 1 |
| titanium dioxide | 5 |
| N-lauroyllysine | 5 |
| red iron oxide | 0.8 |
| yellow iron oxide | 1.2 |
| black iron oxide | 0.1 |
| (Component B) | |
| octyl dodecanol | 1 |
| N-lauloylsarcosine isopropyl ester | 4 |
| silicone | 5 |

FORMULATION EXAMPLE 54

Solid Face Powder

A solid face powder was prepared in a usual manner according to the composition shown in Table 50 below. That is, the components under Component A were mixed using a blender, and the components under Component B were added thereto to adjust the color. These were uniformly mixed. The mixture was pulverized using a mill, and compression-molded in an inside dish. This solid powder had a good pigment dispersion state without color unevenness, and was also excellent in feeling upon use.

TABLE 50

| Solid face powder | |
|---|---|
| (Component A) | |
| talc | 54.0% |
| sericite | 14.0 |
| kaolin | 10.0 |
| titanium dioxide | 4.5 |
| zinc myristate | 5.0 |
| magnesium carbonate | 5.0 |
| color pigment | 0.3 |
| (Component B) | |
| N-cocoylsarcosine isopropyl ester | 3.0 |
| squalane | 2.0 |
| glycerol triisooctanoate | 2.0 |
| antiseptic | 0.1 |
| flavor | 0.1 |

FORMULATION EXAMPLE 55

Eye Liner

An eye liner was prepared in a usual manner according to the composition shown in Table 51 below. That is, the Red No. 401, talc and the zinc stearate as pigments, were mixed using a blender. The other components were heat-dissolved, and the former pigment mixture was then added thereto. These were uniformly mixed to obtain a product. This eye liner had a good pigment dispersibility without color unevenness, and was also excellent in feeling upon use.

TABLE 51

| Eye liner | |
|---|---|
| Red No. 401 | 34.5% |
| talc | 10.0 |
| zinc stearate | 4.0 |
| stearic acid | 15.0 |
| bees wax | 3.0 |
| microcrystalline wax | 5.0 |
| hardened oil | 3.0 |
| N-lauroylglutamic acid isopropyl diester | 3.5 |
| cetyl isostearate | 5.0 |
| Japan wax | 17.0 |

FORMULATION EXAMPLE 56

Eye Shadow

An eye shadow was prepared in a usual manner according to the composition shown in Table 52 below. That is, needle-like titanium oxide and Blue No. 1 were mixed well using a blender. The other components were heat-dissolved. The pigments treated above were added thereto, and these were uniformly dispersed. After the completion of the dispersing operation, the dispersion was poured into a mold for molding. This eye shadow had a good pigment dispersion state without color unevenness, and was also excellent in feeling upon use.

TABLE 52

| Eye shadow | |
|---|---|
| bees wax | 5.0% |
| carnauba wax | 4.0 |
| candelilla wax | 6.0 |
| ceresine | 10.0 |
| microcrystalline wax | 8.0 |
| castor oil | 31.0 |
| N-cocoylalanine isopropyl ester | 9.0 |
| hexadecyl isostearate | 5.0 |
| liquid lanoline | 3.0 |
| sorbitan monooleate | 1.0 |
| needle-like titanium oxide | 3.0 |
| talc | 5.0 |
| Blue No. 1 | 10.0 |

FORMULATION EXAMPLE 57

Lipstick

A lipstick was prepared in a usual manner according to the composition shown in Table 53 below. That is, stick-like titanium oxide and Red No. 202 were added to a castor oil and a part of N-lauroyl-N-methyl-β-alanine isopropyl ester, and treated using a roller. The other components were heat-dissolved, and the above-treated pigments were then added thereto. These were uniformly dispersed using a homomixer. After the completion of the dispersing operation, the dispersion was poured into a mold, and rapidly cooled to form a stick. This lipstick had a good pigment dispersion state without color unevenness, and was also excellent in feeling upon use.

TABLE 53

| Lipstick | |
|---|---|
| bees wax | 7.0% |
| candelilla wax | 7.0 |
| carnauba wax | 2.0 |
| ceresine | 10.0 |
| microcrystalline wax | 6.0 |
| castor oil | 45.0 |
| lanoline | 8.0 |
| octyldodecyl ricinoleate | 2.0 |
| N-lauroyl-N-methyl-β-alanine isopropyl ester | 5.0 |
| stick-like titanium oxide | 2.5 |
| Red No. 202 | 5.5 |

INDUSTRIAL APPLICABILITY

The cosmetic composition containing the N-long-chain acyl neutral amino acid ester according to the first invention is excellent in feelings upon use onto the skin, such as clean feeling, extensibility, adaptability, smoothness and the like, and has also an excellent hair conditioning effect.

The N-long-chain neutral or acidic amino acid ester according to the second invention is incorporated as an oily agent (oily material) into a UV absorbing composition, whereby the sparingly-soluble ultraviolet ray absorbent is stabilized without being precipitated during storage, and the ultraviolet ray-absorbing composition which is organoleptically excellent without stickiness or the like can easily be prepared.

According to the third invention, an inorganic pigment composition can easily be obtained which is excellent in dispersion stability of the inorganic pigment and which is also organoleptically excellent without stickiness or the like as a cosmetic composition or the like.

What is claimed is:

1. An oily material for cosmetic compositions which oily material is an N-long-chain acyl neutral amino acid ester containing a straight-chain or branched-chain, saturated or unsaturated acyl group having from 6 to 22 carbon atoms, where the hydrocarbon group of the alcohol constituting said ester is a straight-chain or branched-chain, saturated or unsaturated hydrocarbon group having from 1 to 10 carbon atoms.

2. The oily material for cosmetic compositions as set forth in claim 1, wherein said N-long-chain acyl neutral amino acid ester is represented by the general formula (1) below:

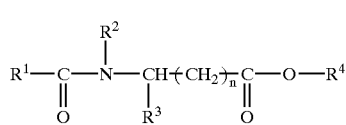

(1)

wherein
$R^1$ represents a branched-chain or straight-chain alkyl or alkenyl group having from 5 to 21 carbon atoms,
$R^2$ represents a hydrogen atom or a straight-chain or branched-chain alkyl group having from 1 to 3 carbon atoms,
$R^3$ represents a hydrogen atom or a straight-chain or branched-chain alkyl group having from 1 to 4 carbon atoms,
$R^4$ represents a branched-chain or straight-chain alkyl or alkenyl group having from 1 to 10 carbon atoms, and
n is an integer of from 0 to 2.

3. A cosmetic composition, comprising at least one oily material for cosmetic compositions as set forth in claim 1 or 2.

4. An N-long-chain acyl neutral amino acid ester which is represented by the general Formula (1) below:

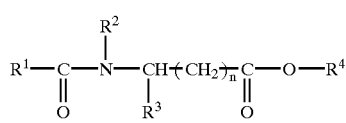

(1)

wherein
$R^1$ represents a branched-chain or straight-chain alkyl or alkenyl group having from 5 to 21 carbon atoms,
$R^2$ represents a hydrogen atom or a straight-chain or branched-chain alkyl group having from 1 to 3 carbon atoms,
$R^3$ represents a hydrogen atom or a straight-chain or branched-chain alkyl group having from 1 to 4 carbon atoms,
$R^4$ represents a branched-chain or straight-chain alkyl or alkenyl group having from 1 to 10 carbon atoms, and
n is an integer of from 0 to 2.

5. An ultraviolet ray-absorbing composition, comprising, as active ingredients, an ultraviolet ray absorbent and a component selected from the group consisting of (A) an N-long-chain acyl neutral amino acid ester containing a straight-chain or branched-chain, saturated or unsaturated acyl group having from 6 to 22 carbon atoms, where the hydrocarbon group of the alcohol constituting said ester is a straight-chain or branched-chain, saturated or unsaturated hydrocarbon group having from 1 to 10 carbon atoms, (B) an N-long-chain acyl acidic amino acid diester containing a straight-chain or branched-chain, saturated or unsaturated acyl group having from 6 to 22 carbon atoms, where the hydrocarbon group of the alcohol constituting said ester is a straight-chain or branched-chain, saturated or unsaturated hydrocarbon group having from 1 to 10 carbon atoms, and mixtures thereof.

6. An inorganic pigment composition, composition, as active ingredients, an inorganic pigment and a component selected from the group consisting of (A) an N-long-chain acyl neutral amino acid ester containing a straight-chain or branched-chain, saturated or unsaturated acyl group having from 6 to 22 carbon atoms, where the hydrocarbon group of the alcohol constituting said ester is a straight-chain or branched-chain, saturated or unsaturated hydrocarbon group having from 1 to 10 carbon atoms, (B) an N-long-chain acyl acidic amino acid diester containing a straight-chain or branched-chain, saturated or unsaturated acyl group having from 6 to 22 carbon atoms, where the hydrocarbon group of the alcohol constituting said ester is a straight-chain or branched-chain, saturated or unsaturated hydrocarbon group having from 1 to 10 carbon atoms, and mixtures thereof.

7. The inorganic pigment composition as set forth in claim 6, wherein the surfaces of the inorganic pigment particles are coated with at least one of said N-long-chain acyl amino acid esters.

8. The composition of claim 3, wherein the oily material is present in an amount of 0.01% by weight or more based on the weight of the composition.

9. The composition of claim 3, wherein the oily material is present in an amount of 0.1–50% by weight based on the weight of the composition.

10. The composition of claim 3, wherein the oily material is present in an amount of 0.1–30% by weight based on the weight of the composition.

11. The composition of claim 5, wherein the ultraviolet ray absorbent is present in an amount of 0.01–50% by weight, based on the weight of the composition.

12. The composition of claim 5, wherein the ultraviolet ray absorbent is present in an amount of 0.1–20% by weight, based on the weight of the composition.

13. The composition of claim 6, wherein the N-long-chain acyl amino acid ester is present in an amount of 1–5% by weight based on the inorganic pigment.

14. The composition of claim 6, wherein the inorganic pigment is present in an amount of 0.01–90% by weight, based on the weight of the composition.

15. The composition of claim 6, wherein a ratio of (inorganic pigment)/(N-long-chain acyl amino acid ester)= 100/0.1 to 1/100.

16. The N-long-chain acyl neutral amino acid ester of claim 4, wherein n is 1.

17. The N-long-chain acyl neutral amino acid ester of claim 4, wherein n is 2.

* * * * *